US010821167B2

(12) United States Patent
Hall et al.

(10) Patent No.: US 10,821,167 B2
(45) Date of Patent: Nov. 3, 2020

(54) **VLP-BASED VACCINES FOR TARGETING *STAPHYLOCOCCUS AUREUS* SECRETED VIRULENCE FACTORS**

(71) Applicant: STC.UNM, Albuquerque, NM (US)

(72) Inventors: Pamela Hall, Albuquerque, NM (US); Bryce Chackerian, Albuquerque, NM (US); David S. Peabody, Albuquerque, NM (US); Seth Michael Daly, Albuquerque, NM (US); Bradley Owen Elmore, Worthington, MN (US); Kathleen Triplett, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

(21) Appl. No.: 16/074,886

(22) PCT Filed: Feb. 1, 2017

(86) PCT No.: PCT/US2017/015960
§ 371 (c)(1),
(2) Date: Aug. 2, 2018

(87) PCT Pub. No.: WO2017/136400
PCT Pub. Date: Aug. 10, 2017

(65) Prior Publication Data
US 2019/0038735 A1 Feb. 7, 2019

Related U.S. Application Data

(60) Provisional application No. 62/290,092, filed on Feb. 2, 2016.

(51) Int. Cl.
| | | |
|---|---|---|
| *C12Q 1/68* | (2018.01) | |
| *A61K 39/085* | (2006.01) | |
| *A61P 37/04* | (2006.01) | |
| *A61P 31/04* | (2006.01) | |
| *A61K 39/00* | (2006.01) | |

(52) U.S. Cl.
CPC ........... *A61K 39/085* (2013.01); *A61P 31/04* (2018.01); *A61P 37/04* (2018.01); *A61K 2039/52* (2013.01); *A61K 2039/5258* (2013.01); *C12N 2795/18123* (2013.01)

(58) Field of Classification Search
None
See application file for complete search history.

(56) References Cited

U.S. PATENT DOCUMENTS 9,394,371 B2 * 7/2016 Janda ................ C07K 16/44

FOREIGN PATENT DOCUMENTS

| WO | WO-9744349 A1 * | 11/1997 | ............ C07K 14/31 |
| WO | WO-9926968 A1 * | 6/1999 | ............... C07K 7/06 |
| WO | WO-2004082701 A1 * | 9/2004 | ............... C07K 7/06 |
| WO | WO-2009055054 A2 * | 4/2009 | ........... A61K 39/085 |
| WO | 2013106525 A1 | 7/2013 | |

OTHER PUBLICATIONS

Greenspan et al (Nature Biotechnology 7: 936-937, 1999).*
Chothia et al (The EMBO Journal, 1986, 5/4:823-26).*
Chackerian, B.; Virus-like particles: flexible platforms for vaccine development. Expert Review of Vaccines 2007, vol. 6, No. 3, pp. 381-390.
O'Rourke, John P. et al.; Development of a Mimotope Vaccine Targeting the *Staphylococcus aureus* Quorum Sensing Pathway. PLoS One 2014, vol. 9, No. 11, pp. 1-8. e111198. doi:10.1371/journal.pone.0111198, p. 1-8.
Lee, G. C. et al. Incidence and Cost of Skin and soft Tissue Infections in the united States. Value Health 18, doi:10.1016/j.jval.2015.03.1424 (2015).
Moran, G. J. et al. Methicillin-resistant *S. aureus* infections among patients in the emergency department. N. Engl. J. Med. 355, 666-674, doi:10.1056/NEJMoa055356 (2006).
Talan, D. A. et al. Comparison of *Staphylococcus aureus* from skin and soft-tissue infections in US emergency department patients, 2004 and 2008. Clin. Infect. Dis. 53, 144-149, doi:10.1093/cid/cir308 (2011).
Labreche, M. J. et al. Treatment failure and costs in patients with methicillin-resistant *Staphylococcus aureus* (MRSA) skin and soft tissue infections: a South Texas Ambulatory Research Network (STARNet) study. J. Am. Board Fam. Med. 26, 508-517, doi:10.3122/jabfm.2013.05.120247 (2013).
Montgomery, C. P., David, M. Z. & Daum, R. S. Host factors that contribute to recurrent staphylococcal skin infection. Curr. Opin. Infect. Dis. 28, 253-258, doi:10.1097/QCO.0000000000000156 (2015).
Fowler, V. G., Jr. & Proctor, R. A. Where does a *Staphylococcus aureus* vaccine stand? Clin. Microbiol. Infect. 20 Suppl 5, 66-75, doi:10.1111/1469-0691.12570 (2014).
Cheung, G. Y., Wang, R., Khan, B. A., Sturdevant, D. E. & Otto, M. Role of the accessory gene regulator agr in community-associated methicillin-resistant *Staphylococcus aureus* pathogenesis. Infect. Immun. 79, 1927-1935, doi:10.1128/IAI.00046-11 (2011).
Montgomery, C. P., Boyle-Vavra, S. & Daum, R. S. Importance of the global regulators Agr and SaeRS in the pathogenesis of CA-MRSA USA300 infection. PLoS One 5, e15177, doi:10.1371/journal.pone.0015177 (2010).

(Continued)

*Primary Examiner* — Jennifer E Graser
(74) *Attorney, Agent, or Firm* — Henry D. Coleman; R. Neil Sudol

(57) ABSTRACT

The present invention is directed to virus-like particles (VLPs) which are engineered to present epitopes from *Staphylococcus aureus* (SA), preferably autoinducing peptides (AIPs) which regulate quorum-sensing dependent virulence in this pathogen, or epitopes from SA toxins and leukocidins. These VLPs may be used to provide immunogenic compositions and efficacious vaccines. In a mouse model of SA dermonecrosis, vaccination with AIP-containing VLPs or SA toxin-containing VLPs induces protective immunity to limit the pathogenesis of SA infection and promote bacterial clearance.

20 Claims, 15 Drawing Sheets

Specification includes a Sequence Listing.

(56) References Cited

OTHER PUBLICATIONS

Novick, R. P. & Geisinger, E. Quorum sensing in staphylococci. Annu. Rev. Genet. 42, 541-564, doi:10.1146/annurev.genet.42.110807.091640 (2008).
Thoendel, M., Kavanaugh, J. S., Flack, C. E. & Horswill, A. R. Peptide signaling in the *Staphylococci*. Chem. Rev. 111, 117-151, doi:10.1021/cr100370n (2011).
Kaufmann, G. F., Park, J. & Janda, K. D. Bacterial quorum sensing: a new target for anti-infective immunotherapy. Expert Opin. Biol. Ther. 8, 719-724, doi:10.1517/14712598.8.6.719 (2008).
Park, J. et al. Infection control by antibody disruption of bacterial quorum sensing signaling. Chem. Biol. 14, 1119-1127, doi:10.1016/j.chembiol.2007.08.013 (2007).
O'Rourke, J. P. et al. Development of a mimotope vaccine targeting the *Staphylococcus aureus* quorum sensing pathway. PLoS One 9; e111198, doi:10.1371/journal.pone.0111198 (2014).
Jarraud, S. et al. Relationships between *Staphylococcus aureus* genetic background, virulence factors, agr groups (Alleles), and human disease. Infect Immun. 70, 631-641, doi:Doi 10.1128/Iai.70.2.631-641.2002 (2002).
Traber, K. E. et al. agr function in clinical *Staphylococcus aureus* isolates. Microbiology 154, 2265-2274, doi:10.1099/mic.0.2007/011874-0 (2008).
Kaufmann, G. F., Park, J., Mayorov, A. V., Kubitz, D. M. & Janda, K. D. Generation of quorum quenching antibodies. Methods Mol. Biol. 692, 299-311, doi:10.1007/978-1-60761-971-0_22 (2011).
Chackerian, B. Virus-like particles: flexible platforms for vaccine development. Expert review of vaccines 6, 381-390 (2007).
Caldeira, J. C. & Peabody, D. S. Thermal stability of RNA phage virus-like particles displaying foreign peptides. Journal of nanobiotechnology 9, 22/3155-3159-3122 (2011).
Caldeira, J. C. & Peabody, D. S. Stability and assembly in vitro of bacteriophage PP7 virus-like particles. J Nanobiotechnology 5, 10, doi:10.1186/1477-3155-5-10 (2007).
Caldeira Jdo, C. et al. Immunogenic display of diverse peptides, including a broadly cross-type neutralizing human papillomavirus L2 epitope, on virus-like particles of the RNA bacteriophage PP7. Vaccine 28, 4384-4393, doi:10.1016/j.vaccine.2010.04.049 (2010).
Chao, J. A., Patskovsky, Y., Almo, S. C. & Singer, R. H. Structural basis for the coevolution of a viral RNA-protein complex. Nat. Struct. Mol. Biol. 15, 103-105, doi:10.1038/nsmb1327 (2008).
Wright, J. S., 3rd, Jin, R. & Novick, R. P. Transient interference with staphylococcal quorum sensing blocks abscess formation. Proc. Natl. Acad. Sci. U. S. A. 102, 1691-1696, doi:10.1073/pnas.0407661102 (2005).
Peterson, M. M. et al. Apolipoprotein B Is an innate barrier against invasive *Staphylococcus aureus* infection. Cell Host Microbe 4, 555-566, doi:10.1016/j.chom.2008.10.001 (2008).
Sully, E. K. et al. Selective chemical inhibition of agr quorum sensing in *Staphylococcus aureus* promotes host defense with minimal impact on resistance. PLoS Pathog. 10, e1004174, doi:10.1371/journal.ppat.1004174 (2014).
Hall, P. R. et al. Nox2 modification of LDL is essential for optimal apolipoprotein B-mediated control of agr type III *Staphylococcus aureus* quorum-sensing. PLoS Pathog. 9, e1003166, doi:10.1371/journal.ppat.1003166 (2013).
Daly, S. M. et al. omega-Hydroxyemodin limits *Staphylococcus aureus* quorum sensing-mediated pathogenesis and inflammation. Antimicrob. Agents Chemother. 59, 2223-2235, doi:10.1128/AAC.04564-14 (2015).
Gray, B., Hall, P. & Gresham, H. Targeting agr- and agr-Like quorum sensing systems for development of common therapeutics to treat multiple gram-positive bacterial infections. Sensors 13, 5130-5166, doi:10.3390/s130405130 (2013).
Tars, K., Fridborg, K., Bundule, M. & Liljas, L. The three-dimensional structure of bacteriophage PP7 from Pseudomonas aeruginosa at 3.7-A resolution. Virology 272, 331-337, doi:10.1006/viro.2000.0373 (2000).

Tars, K., Fridborg, K., Bundule, M. & Liljas, L. Structure determination of bacteriophage PP7 from Pseudomonas aeruginosa: from poor data to a good map. Acta Crystallogr. D Biol. Crystallogr. 56, 398-405 (2000).
Tumban, E., Peabody, J., Peabody, D. S. & Chackerian, B. A pan-HPV vaccine based on bacteriophage PP7 VLPs displaying broadly cross-neutralizing epitopes from the HPV minor capsid protein, L2. PLoS One 6 (2011).
Ko, J., Park, H., Heo, L. & Seok, C. GalaxyWEB server for protein structure prediction and refinement. Nucleic Acids Res. 40, W294-297, doi:10.1093/nar/gks493 (2012).
Park, H., Lee, G. R., Heo, L. & Seok, C. Protein loop modeling using a new hybrid energy function and its application to modeling in inaccurate structural environments. PLoS One 9, e113811, doi:10.1371/journal.pone.0113811 (2014).
Carrel, M., Perencevich, E. N. & David, M. Z. USA300 Methicillin-Resistant *Staphylococcus aureus*, United States, 2000-2013. Emerg. Infect. Dis. 21, 1973-1980, doi:10.3201/eid2111.150452 (2015).
Rynda-Apple, A. et al. Virus-like particle-induced protection against MRSA pneumonia is dependent on IL-13 and enhancement of phagocyte function. The American journal of pathology 181, 196-210 (2012).
Malachowa, N., Kobayashi, S. D., Braughton, K. R. & DeLeo, F. R. Mouse model of *Staphylococcus aureus* skin infection. Methods Mol. Biol. 1031, 109-116, doi:10.1007/978-1-62703-481-4_14 (2013).
Public health dispatch: outbreaks of community-associated methicillin-resistant *Staphylococcus aureus* skin infections—Los Angeles County, California, 2002-2003. Can. Commun. Dis. Rep. 29, 110-112 (2003).
Inoshima, N., Wang, Y. & Bubeck Wardenburg, J. Genetic requirement for ADAM10 in severe *Staphylococcus aureus* skin infection. J. Invest. Dermatol. 132, 1513-1516, doi:10.1038/jid.2011.462 (2012).
Kennedy, A. D. et al. Targeting of alpha-hemolysin by active or passive immunization decreases severity of USA300 skin infection in a mouse model. J Infect Dis 202, 1050-1058, doi:10.1086/656043 (2010).
Sampedro, G. R. et al. Targeting *Staphylococcus aureus* alpha-toxin as a novel approach to reduce severity of recurrent skin and soft-tissue infections. J Infect Dis 210, 1012-1018, doi:10.1093/infdis/jiu223 (2014).
Kobayashi, S. D. et al. Comparative analysis of USA300 virulence determinants in a rabbit model of skin and soft tissue infection. J Infect Dis 204, 937-941, doi:10.1093/infdis/jir441 (2011).
Berube, B. J. & Bubeck Wardenburg, J. *Staphylococcus aureus* alpha-toxin: nearly a century of intrigue. Toxins (Basel) 5, 1140-1166 (2013).
NIAID Antimicrobial Resistance Program: Current Status and Future Directions 2014—ARstrategicplan2014.pdf, <www.ncbi.nlm.nih.gov/pubmed/> (2015).
Spellberg, B., Bartlett, J. G. & Gilbert, D. N. The future of antibiotics and resistance. N. Engl. J. Med. 368, 299-302, doi:10.1056/NEJMp1215093 (2013).
DeLeo, F. R., Diep, B. A. & Otto, M. Host defense and pathogenesis in *Staphylococcus aureus* infections. Infect. Dis. Clin. North Am. 23, 17-34 (2009).
Cheung, G. Y. & Otto, M. The potential use of toxin antibodies as a strategy for controlling acute *Staphylococcus aureus* infections. Expert Opin. Ther. Targets 16, 601-612 (2012).
Tkaczyk, C. et al. *Staphylococcus aureus* alpha toxin suppresses effective innate and adaptive immune responses in a murine dermonecrosis model. PLoS One 8, e75103, doi:10.1371/journal.pone.0075103 (2013).
Proctor, R. A. Recent developments for *Staphylococcus aureus* vaccines: clinical and basic science challenges. European cells & materials 30, 315-326 (2015).
Berube, B. J. & Wardenburg, J. B. *Staphylococcus aureus* alpha-Toxin: Nearly a Century of Intrigue. Toxins (Basel) 5, 1140-1166, doi:DOI 10.3390/toxins5061140 (2013).
Bubeck Wardenburg, J. & Schneewind, O. Vaccine protection against *Staphylococcus aureus* pneumonia. J. Exp.Med. 205, 287-294, doi:10.1084/jem.20072208 (2008).
Adhikari, R. P. et al. Novel structurally designed vaccine for *S. aureus* alpha-hemolysin: protection against bacteremia and pneumonia. PLoS One 7, e38567, doi:10.1371/journal.po-ne.003-8587 (2012).

(56) References Cited

OTHER PUBLICATIONS

Oscherwitz, J., Munoz-Planillo, R., Yu, F., Nunez, G. & Cease, K. B. In vivo mapping of a protective linear neutralizing epitope at the N-terminus of alpha hemolysin from *Staphylococcus aureus*. Mol. Immunol. 60, 62-71 (2014).
Oscherwitz, J. & Cease, K. B. Identification and validation of a linear protective neutralizing epitope in the beta-pore domain of alpha toxin. PLoS One 10, e0116882, doi:10.1371/journal.pone.0116882 (2015).
Yu, X. Q. et al. Safety, Tolerability, and Pharmacokinetics of MEDI4893, an Investigational, ExtendedHalf-Life, Anti-*Staphylococcus aureus* Alpha-Toxin Human Monoclonal Antibody, in Healthy Adults. Antimicrob. Agents Chemother., doi:10.1128/aac.01020-16 (2016).
Figueroa, M. et al. Polyhydroxyanthraquinones as Quorum Sensing Inhibitors from the Guttates of Penicillium restrictum and Their Analysis by Desorption Electrospray Ionization Mass Spectrometry. J. Nat. Prod. 77, 1351-1358, doi:Doi 10.1021/Np5000704 (2014).
Khodaverdian, V. et al. Discovery of Antivirulence Agents against Methicillin-Resistant *Staphylococcus aureus*. Antimicrob. Agents Chemother. 57, 3645-3652 (2013).
Kuo, D. et al. Novel quorum-quenching agents promote methicillin-resistant *Staphylococcus aureus* (MRSA) wound healing and sensitize MRSA to beta-lactam antibiotics. Antimicrob. Agents Chemother. 59, 1512-1518, doi:10.1128/AAC.04767-14 (2015).
Yu, G., Kuo, D., Shoham, M. & Viswanathan, R. Combinatorial synthesis and in vitro evaluation of a biaryl hydroxyketone library as antivirulence agents against MRSA. ACS combinatorial science 16, 85-91, doi:10.1021/co400142t (2014).
Cech, N. B., Junio, H. A., Ackermann, L. W., Kavanaugh, J. S. & Horswill, A. R. Quorum quenching and antimicrobial activity of goldenseal (*Hydrastis canadensis*) against methicillin-resistant *Staphylococcus aureus* (MRSA). Planta Med. 78, 1556-1561, doi:10.1055/s-0032-1315042 (2012).
Quave, C. L. et al. *Castanea sativa* (European Chestnut) Leaf Extracts Rich in Ursene and Oleanene Derivatives Block *Staphylococcus aureus* Virulence and Pathogenesis without Detectable Resistance. PLoS One 10, e0136486, doi:10.1371/journal.pone.0136486 (2015).
Vermote, A. et al. Hamamelitannin Analogues that Modulate Quorum Sensing as Potentiators of Antibiotics against *Staphylococcus aureus*. Angew. Chem. Int. Ed. Engl. 55, 6551-6555, doi:10.1002/anie.201601973 (2016).
Nakayama, J. et al. Ambuic acid inhibits the biosynthesis of cyclic peptide quormones in gram-positive bacteria. Antimicrob Agents Chemother. 53, 580-586, doi:10.1128/AAC.00995-08 (2009).
Tal-Gan, Y., Stacy, D. M., Foegen, M. K., Koenig, D. W. & Blackwell, H. E. Highly potent inhibitors of quorum sensing in *Staphylococcus aureus* revealed through a systematic synthetic study of the group-III autoinducing peptide. J. Am. Chem. Soc. 135, 7869-7882, doi:10.1021/ja3112115 (2013).
Tal-Gan, Y., Ivancic, M., Cornilescu, G., Yang, T. & Blackwell, H. E. Highly Stable, Amide-Bridged Autoinducing Peptide Analogues that Strongly Inhibit the AgrC Quorum Sensing Receptor in *Staphylococcus aureus*. Angew. Chem. Int. Ed. Engl. 55, 8913-8917, doi:10.1002/anie.201602974 (2016).
Gordon, C. P., Williams, P. & Chan, W. C. Attenuating *Staphylococcus aureus* virulence gene regulation: a medicinal chemistry perspective. J. Med. Chem. 56, 1389-1404 (2013).
Murray, E. J. et al. Targeting *Staphylococcus aureus* quorum sensing with nonpeptidic small molecule inhibitors. J. Med. Chem. 57, 2813-2819, doi:10.1021/jm500215s (2014).
Chan, W. C., Coyle, B. J. & Williams, P. Virulence regulation and quorum sensing in staphylococcal infections: competitive AgrC antagonists as quorum sensing inhibitors. J. Med. Chem. 47, 4633-4641, doi:10.1021/jm0400754 (2004).
Kirchdoerfer, R. N. et al. Structural basis for ligand recognition and discrimination of a quorum-quenching antibody. J Biol Chem 286, 17351-17358, doi:10.1074/jbc.M111.231258 (2011).

Freitag, N. E., Port, G. C. & Miner, M. D. Listeria monocytogenes—from saprophyte to intracellular pathogen. Nat. Rev. Microbiol. 7, 623-628, doi:10.1038/nrmicro2171 (2009).
Garmyn, D., Gal, L., Lemaitre, J. P., Hartmann, A. & Piveteau, P. Communication and autoinduction in the species *Listeria monocytogenes*: A central role for the agr system. Commun. Integr. Biol. 2, 371-374 (2009).
Autret, N., Raynaud, C., Dubail, I., Berche, P. & Charbit, A. Identification of the agr locus of Listeria monocytogenes: role in bacterial virulence. Infect. Immun. 71, 4463-4471 (2003).
Riedel, C. U. et al. AgrD-dependent quorum sensing affects biofilm formation, invasion, virulence and global gene expression profiles in Listeria monocytogenes. Mol. Microbiol. 71, 1177-1189, doi:10.1111/j.1365-2958.2008.06589.x (2009).
Rieu, A., Weidmann, S., Garmyn, D., Piveteau, P. & Guzzo, J. Agr system of Listeria monocytogenes EGD-e: role in adherence and differential expression pattern. Appl. Environ. Microbiol. 73, 6125-6133, doi:10.1128/aem.00608-07 (2007).
Rieu, A. et al. Listeria monocytogenes EGD-e biofilms: no mushrooms but a network of knitted chains. Appl. Environ. Microbiol 74, 4491-4497, doi:10.1128/aem.00255-08 (2008).
Zetzmann, M., Sanchez-Kopper, A., Waidmann, M. S., Blombach, B. & Riedel, C. U. Identification of the agr Peptide of Listeria monocytogenes. Front. Microbiol. 7, 989, doi:10.3389/fmicb.2016.00989 (2016).
Gilmore, M. S., Clewell, D. B., Ike, Y. & Shankar, N. Enterococci. (Massachusetts Eye and Ear Infirmary, 2014).
Nakayama, J. et al. Gelatinase biosynthesis-activating pheromone: a peptide lactone that mediates a quorum sensing in Enterococcus faecalis. Mol. Microbiol. 41, 145-154 (2001).
Nakayama, J. et al. Revised model for Enterococcus faecalis fsr quorum-sensing system: the small open reading frame fsrD encodes the gelatinase biosynthesis-activating pheromone propeptide corresponding to staphylococcal agrd. J. Bacteriol. 188, 8321-8326, doi:10.1128/jb.00865-06 (2006).
Cook, L. C. & Federle, M. J. Peptide pheromone signaling in *Streptococcus* and Enterococcus. FEMS Microbiol. Rev. 38, 473-492, doi: 10.1111/1574-6976.12046 (2014).
Hancock, L. E. & Perego, M. The Enterococcus faecalis fsr two-component system controls biofilm development through production of gelatinase. J. Bacteriol. 186, 5629-5639, doi:10.1128/jb.186.17.5629-5639.2004 (2004).
Qin, X., Singh, K. V., Weinstock, G. M. & Murray, B. E. EffectS of Enterococcus faecalis fsr Genes on Production of Gelatinase and a Serine Protease and Virulence. doi:10.1128/IAI.68.5.2579-2586.2000 (2000).
Thurlow, L. R. et al. Gelatinase contributes to the pathogenesis of endocarditis caused by Enterococcus faecalis. Infect Immun. 78, 4936-4943, doi:10.1128/iai.01118-09 (2010).
Engelbert, M., Mylonakis, E., Ausubel, F. M., Calderwood, S. B. & Gilmore, M. S. Contribution of gelatinase, serine protease, and fsr to the pathogenesis of Enterococcus faecalis endophthalmitis. Infect. Immun. 72, 3628-3633, doi:10.1128/iai.72.6.3628-3633.2004 (2004).
Shankar, J., Walker, R.-G., Ward, D. & Horsburgh, M. J. In PLoS One vol. 7 (2012).
Darkoh, C., DuPont, H. L., Norris, S. J. & Kaplan, H. B. Toxin synthesis by Clostridium difficile is regulated through quorum signaling. mBio 6, e02569, doi:10.1128/mBio.02569-14 (2015).
Darkoh, C., Odo, C. & DuPont, H. L. Accessory Gene Regulator-1 Locus Is Essential for Virulence and Pathogenesis of Clostridium difficile. mBio 7, doi:10.1128/mBio.01237-16 (2016).
Kuehne, S. A. et al. The role of toxin A and toxin B in Clostridium difficile infection. Nature 467, 711-713, doi:10.1038/nature09397 (2010).
Cohen, S. H. et al. Clinical practice guidelines for Clostridium difficile infection in adults: 2010 update by the society for healthcare epidemiology of America (SHEA) and the infectious diseases society of America (IDSA). Infect. Control Hosp. Epidemiol. 31, 431-455, doi:10.1086/651706 (2010).
Naskalska, A. & Pyrc, K. Virus Like Particles as Immunogens and Universal Nanocarriers. Pol. J. Microbiol. 64, 3-13 (2015).
Lacson, E. et al. Antibody response to Engerix-B and Recombivax-HB hepatitis B vaccination in end-stage renal disease. Hemodialysis

(56) References Cited

OTHER PUBLICATIONS international. International Symposium on Homa Hemodialysis 9, 367-375, doi:10.1111/j.1492-7535.2005.01155.x (2005).
Gardasilâ®9 (Human Papillomavirus 9-valent Vaccine, Recombinant) for Health Care Professionals, <www.merckvaccines.com/Products/Gardasil9pgid=UoXun1ClyLRSROEK44UuV0Tn0000rKPQB0Nasid=cz3-ITHtiBPklWaMzyyb3i5Babw108qEoIE=> (2016).
Chackerian, B., Durfee, M. R. & Schiller, J. T. Virus-like display of a neo-self antigen reverses B cell anergy in a B cell receptor transgenic mouse model. J Immunol 180, 5816-5825 (2008).
Chackerian, B., Lowy, D. R. & Schiller, J. T. Conjugation of a self-antigen to papillomavirus-like particles allows for efficient induction of protective autoantibodies. J. Clin. Invest 108, 415-423 (2001).
Chackerian, B., Lowy, D. R. & Schiller, J. T. Induction of autoantibodies to mouse CCR5 with recombinant papillomavirus particles. Proc. Natl. Acad. Sci. U. S. A. 96, 2373-2378(1999).
Frietze, K. M., Peabody, D. S. & Chackerian, B. Engineering virus-like particles as vaccine platforms. Curr. Opin. Virol. 18, 44-49, doi:10.1016/j.coviro.2016.03.001 (2016).
Effio, C. L. & Hubbuch, J. Next generation vaccines and vectors: Designing downstream processes for recombinant protein-based virus-like particles. Biotechnology journal 10, 715-727, doi:10.1002/biot.201400392 (2015).
Bachmann, M. F. & Jennings, G. T. Vaccine delivery: a matter of size, geometry, kinetics and molecular patterns. Nature reviews. Immunology 10, 787-796 (2010).
Jennings, G. T. & Bachmann, M. F. Immunodrugs: therapeutic VLP-based vaccines for chronic diseases. Annu. Rev. Pharmacol. Toxicol. 49, 303-326 (2009).
Rivera-Hernandez, T. et al. Self-adjuvanting modular virus-like particles for mucosal vaccination against group A *Streptococcus* (GAS). Vaccine 31, 1950-1955, doi:10.1016/j.vaccine.2013.02.013 (2013).
Seth, A. et al. Modular virus-like particles for sublingual vaccination against group A *Streptococcus*. Vaccine, doi:10.1016/j.vaccine.2016.11.008 (2016).
Tamborrini, M. et al. A Synthetic Virus-Like Particle Streptococcal Vaccine Candidate Using B-Cell Epitopes from the Proline-Rich Region of Pheumococcal Surface Protein A. Vaccines 3, 850-874, doi:10.3390/vaccines3040850 (2015).
Alksne, L. E. & Projan, S. J. Bacterial virulence as a target for antimicrobial chemotherapy. Curr. Opin. Biotechnol. 11, 625-636, doi:Doi 10.1016/30958-1669(00)00155-5 (2000).
In National Research Council (US) Committee for the Update of the Guide for theCare and Use of Laboratory Animals (National Academies Press (US), 2011).
Rothfork, J. M., Dessus-Babus, S., Wamel, W. J. V., Cheung, A. L. & Gresham, H. D. Fibrinogen depletion attenuates *Staphyloccocus aureus* infection by preventing density-dependent virulence gene up-regulation. J Immunol 171, 5389-5395 (2003).
Schneider, C. A., Rasband, W. S. & Eliceiri, K. W. NIH Image to ImageJ: 25 years of image analysis. Nat. Methods 9, (2012). 671-675.
RNA Bacteriophages, in The bacteriophages. Calendar, R L, ed. Oxford University Press. 2005.
Beckett et al.; 1988; J. Mol. Biol. vol. 204; pp. 939-947.
Peabody, D.S.; 1990; J. Biol. Chem. vol. 265; pp. 5684-5689.
GeneBank Accession Nos. 2QUXR; 2UXO/ 2QUX_L; 2QUX_I; 2QUX_F; and 2QUX_C.
Peabody et al.; RNA recognition site of PP7 coat protein, Nucleic Acids Research, 2002, vol. 30, No. 19, pp. 4138-4144.
BESTFIT algorithm in the GCG package, version 10.2, Madison, Wisconsin.
Blastp program of the BLAST2 search algorithm as described by Tatusova et al.; FEMS Microbial Lett.; 1999; vol. 174; pp. 247-250. available at www.ncbi.nlm.nih.gov/blast/bl2seq/bl2.html.
National Research Council of the National Academies, "Guide for the Care and Use of Laboratory Animals", 8th edition; The National Academies Press, Washington, D.C.; www.nap.edu.

\* cited by examiner

FIGURE 1

S. aureus AIP1 C4S variant cloned into AB loop of PP7

PP7-AB loop display upstream primer with AIP1 C4S variant

```
         G   T   Y   S   T   S   D   F   I   M   E   A   T
5'-GGC GGT ACC TAC AGT ACC TCT GAC TTC ATC ATG GAG GCT ACT
        KpnI

R   T   L   T   E
CGC ACT CTG ACT GAG-3'
```

FIGURE 11
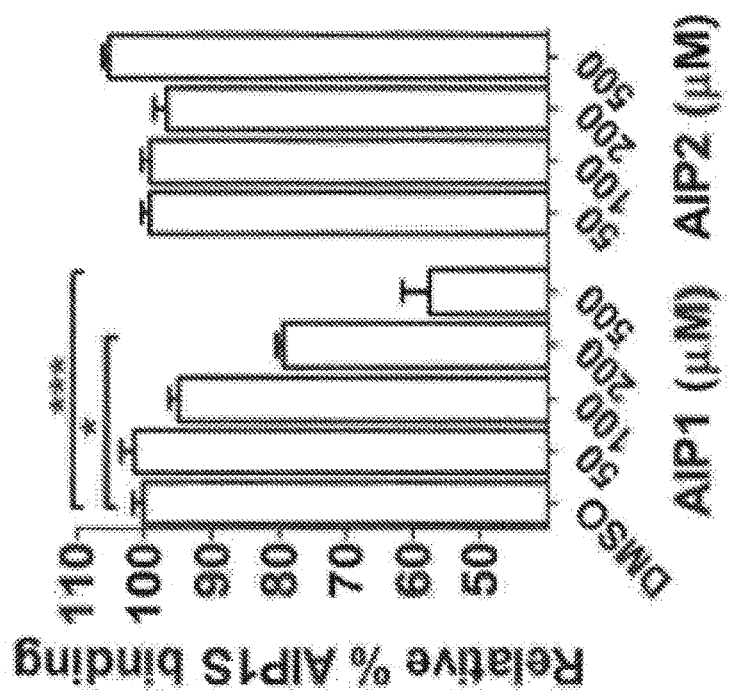
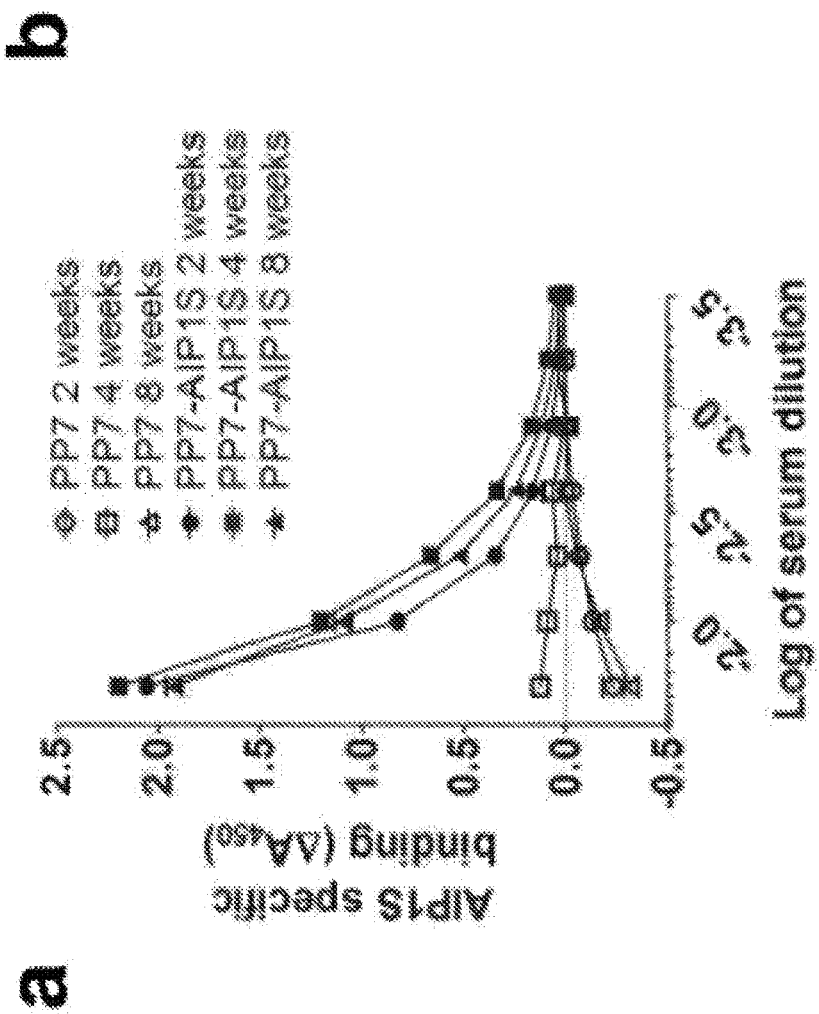

SEQUENCE LISTING

```
<160> NUMBER OF SEQ ID NOS: 39

<210> SEQ ID NO 1
<211> LENGTH: 8
<212> TYPE: PRT
<213> ORGANISM: Staphylococcus aureus

<400> SEQUENCE: 1

Tyr Ser Thr Cys Asp Phe Ile Met
1               5

<210> SEQ ID NO 2
<211> LENGTH: 8
<212> TYPE: PRT
<213> ORGANISM: Artificial
<220> FEATURE:
<223> OTHER INFORMATION: AIP1S

<400> SEQUENCE: 2

Tyr Ser Thr Ser Asp Phe Ile Met
1               5

<210> SEQ ID NO 3
<211> LENGTH: 9
<212> TYPE: PRT
<213> ORGANISM: Staphylococcus aureus

<400> SEQUENCE: 3

Gly Val Asn Ala Cys Ser Ser Leu Phe
1               5

<210> SEQ ID NO 4
<211> LENGTH: 9
```

```
<212> TYPE: PRT
<213> ORGANISM: Artificial
<220> FEATURE:
<223> OTHER INFORMATION: AIP2S

<400> SEQUENCE: 4

Gly Val Asn Ala Ser Ser Ser Leu Phe
1               5

<210> SEQ ID NO 5
<211> LENGTH: 7
<212> TYPE: PRT
<213> ORGANISM: Staphylococcus aureus

<400> SEQUENCE: 5

Ile Asn Cys Asp Phe Leu Leu
1               5

<210> SEQ ID NO 6
<211> LENGTH: 7
<212> TYPE: PRT
<213> ORGANISM: Artificial
<220> FEATURE:
<223> OTHER INFORMATION: AIP3S

<400> SEQUENCE: 6

Ile Asn Ser Asp Phe Leu Leu
1               5

<210> SEQ ID NO 7
<211> LENGTH: 8
<212> TYPE: PRT
<213> ORGANISM: Staphylococcus aureus

<400> SEQUENCE: 7

Tyr Ser Thr Cys Tyr Phe Ile Met
1               5

<210> SEQ ID NO 8
<211> LENGTH: 8
<212> TYPE: PRT
<213> ORGANISM: Artificial
<220> FEATURE:
<223> OTHER INFORMATION: AIP4S

<400> SEQUENCE: 8

Tyr Ser Thr Ser Tyr Phe Ile Met
1               5

<210> SEQ ID NO 9
<211> LENGTH: 54
<212> TYPE: PRT
<213> ORGANISM: Staphylococcus aureus

<400> SEQUENCE: 9

Ile Asn Tyr Leu Pro Lys Asn Lys Ile Asp Ser Val Asn Val Ser Gln
1               5                   10                  15

Thr Leu Gly Tyr Asn Ile Gly Gly Asn Phe Asn Ser Gly Pro Ser Thr
            20                  25                  30

Gly Gly Asn Gly Ser Phe Asn Tyr Ser Lys Thr Thr Ile Ser Tyr Asn
        35                  40                  45

Gln Gln Asn Tyr Ile Ser
    50
```

```
<210> SEQ ID NO 10
<211> LENGTH: 8
<212> TYPE: PRT
<213> ORGANISM: Staphylococcus aureus

<400> SEQUENCE: 10

Lys Trp Gly Val Thr Gln Asn Ile
1               5

<210> SEQ ID NO 11
<211> LENGTH: 54
<212> TYPE: PRT
<213> ORGANISM: Staphylococcus aureus

<400> SEQUENCE: 11

Val Asp Tyr Ala Pro Lys Asn Gln Asn Glu Glu Phe Gln Val Gln Gln
1               5                   10                  15

Thr Val Gly Tyr Ser Tyr Gly Gly Asp Ile Asn Ile Ser Asn Gly Leu
            20                  25                  30

Ser Gly Gly Gly Asn Gly Ser Lys Ser Phe Ser Glu Thr Ile Asn Tyr
        35                  40                  45

Gln Glu Ser Tyr Arg Thr
    50

<210> SEQ ID NO 12
<211> LENGTH: 7
<212> TYPE: PRT
<213> ORGANISM: Staphylococcus aureus

<400> SEQUENCE: 12

Leu Lys Ile Ser Gln Ile Leu
1               5

<210> SEQ ID NO 13
<211> LENGTH: 34
<212> TYPE: PRT
<213> ORGANISM: Staphylococcus aureus

<400> SEQUENCE: 13

Ser Thr Leu Thr Tyr Gly Phe Asn Gly Asn Val Thr Gly Asp Asp Thr
1               5                   10                  15

Gly Lys Ile Gly Gly Leu Ile Gly Ala Asn Val Ser Ile Gly His Thr
            20                  25                  30

Leu Lys

<210> SEQ ID NO 14
<211> LENGTH: 8
<212> TYPE: PRT
<213> ORGANISM: Staphylococcus aureus

<400> SEQUENCE: 14

Glu Asn Gly Met His Lys Lys Val
1               5

<210> SEQ ID NO 15
<211> LENGTH: 13
<212> TYPE: PRT
<213> ORGANISM: Staphylococcus aureus

<400> SEQUENCE: 15

Ser Asp Tyr Tyr Pro Arg Asn Ser Ile Asp Lys Glu Tyr
1               5                   10
```

```
<210> SEQ ID NO 16
<211> LENGTH: 9
<212> TYPE: PRT
<213> ORGANISM: Staphylococcus aureus

<400> SEQUENCE: 16

Lys Tyr Val Gln Pro Asp Phe Lys Thr
1               5

<210> SEQ ID NO 17
<211> LENGTH: 53
<212> TYPE: PRT
<213> ORGANISM: Staphylococcus aureus

<400> SEQUENCE: 17

Ile Asn Tyr Leu Pro Lys Asn Lys Ile Asp Ser Ala Asp Val Ser Gln
1               5                   10                  15

Lys Leu Gly Tyr Asn Ile Gly Gly Asn Phe Gln Ser Ala Pro Ser Ile
                20                  25                  30

Gly Gly Ser Gly Ser Phe Asn Tyr Ser Lys Thr Ile Ser Tyr Asn Gln
            35                  40                  45

Lys Asn Tyr Val Thr
    50

<210> SEQ ID NO 18
<211> LENGTH: 8
<212> TYPE: PRT
<213> ORGANISM: Staphylococcus aureus

<400> SEQUENCE: 18

Arg Leu Ala Ile Thr Gln Asn Ile
1               5

<210> SEQ ID NO 19
<211> LENGTH: 55
<212> TYPE: PRT
<213> ORGANISM: Staphylococcus aureus

<400> SEQUENCE: 19

Val Asp Tyr Ala Pro Lys Asn Gln Asn Glu Glu Phe Gln Val Gln Asn
1               5                   10                  15

Thr Leu Gly Tyr Thr Phe Gly Asp Ile Ser Ile Ser Asn Gly Leu
                20                  25                  30

Ser Gly Gly Leu Asn Gly Asn Thr Ala Phe Ser Glu Thr Ile Asn Tyr
            35                  40                  45

Lys Gln Glu Ser Tyr Arg Thr
    50                  55

<210> SEQ ID NO 20
<211> LENGTH: 7
<212> TYPE: PRT
<213> ORGANISM: Staphylococcus aureus

<400> SEQUENCE: 20

Phe Lys Ile Ser Gln Ile Leu
1               5

<210> SEQ ID NO 21
<211> LENGTH: 53
<212> TYPE: PRT
<213> ORGANISM: Staphylococcus aureus
```

```
<400> SEQUENCE: 21

Ile Asn Tyr Leu Pro Lys Asn Lys Ile Glu Ser Thr Asn Val Ser Gln
1               5                   10                  15

Thr Leu Gly Tyr Asn Ile Gly Gly Asn Phe Gln Ser Ala Pro Ser Leu
            20                  25                  30

Gly Gly Asn Gly Ser Phe Asn Tyr Ser Lys Ser Ile Ser Tyr Thr Gln
        35                  40                  45

Gln Asn Tyr Val Ser
        50

<210> SEQ ID NO 22
<211> LENGTH: 8
<212> TYPE: PRT
<213> ORGANISM: Staphylococcus aureus

<400> SEQUENCE: 22

Lys Trp Gly Val Thr Gln Asn Ile
1               5

<210> SEQ ID NO 23
<211> LENGTH: 54
<212> TYPE: PRT
<213> ORGANISM: Staphylococcus aureus

<400> SEQUENCE: 23

Ile Asn Tyr Leu Pro Lys Asn Lys Ile Glu Thr Thr Asp Val Gly Gln
1               5                   10                  15

Thr Leu Gly Tyr Asn Ile Gly Gly Asn Phe Phe Gln Ser Ala Pro Ser
            20                  25                  30

Ile Gly Gly Asn Gly Ser Phe Asn Tyr Ser Lys Thr Ile Ser Tyr Thr
        35                  40                  45

Gln Lys Ser Tyr Val Ser
        50

<210> SEQ ID NO 24
<211> LENGTH: 8
<212> TYPE: PRT
<213> ORGANISM: Staphylococcus aureus

<400> SEQUENCE: 24

Lys Trp Gly Val Thr Gln Asn Val
1               5

<210> SEQ ID NO 25
<211> LENGTH: 55
<212> TYPE: PRT
<213> ORGANISM: Staphylococcus aureus

<400> SEQUENCE: 25

Val Asp Tyr Ala Pro Lys Asn Gln Asn Glu Glu Phe Gln Val Gln Gln
1               5                   10                  15

Thr Leu Gly Tyr Ser Tyr Gly Gly Asp Ile Asn Ile Ser Asn Gly Leu
            20                  25                  30

Ser Gly Gly Leu Asn Gly Ser Lys Ser Phe Ser Glu Thr Ile Asn Tyr
        35                  40                  45

Lys Gln Glu Ser Tyr Arg Thr
        50                  55

<210> SEQ ID NO 26
<211> LENGTH: 7
```

```
<212> TYPE: PRT
<213> ORGANISM: Staphylococcus aureus

<400> SEQUENCE: 26

Leu Asn Ile Phe Gln Ile Leu
1               5

<210> SEQ ID NO 27
<211> LENGTH: 56
<212> TYPE: PRT
<213> ORGANISM: Staphylococcus aureus

<400> SEQUENCE: 27

Thr Asp Phe Ala Pro Lys Asn Gln Asp Glu Ser Arg Glu Val Lys Tyr
1               5                   10                  15

Thr Tyr Gly Tyr Lys Thr Gly Gly Asp Phe Ser Ile Asn Arg Gly Gly
            20                  25                  30

Leu Thr Gly Asn Ile Thr Lys Glu Ser Asn Tyr Ser Glu Thr Ile Ser
        35                  40                  45

Tyr Gln Gln Pro Ser Tyr Arg Thr
    50                  55

<210> SEQ ID NO 28
<211> LENGTH: 7
<212> TYPE: PRT
<213> ORGANISM: Staphylococcus aureus

<400> SEQUENCE: 28

Lys Asn Ile Thr Gln Ser Leu
1               5

<210> SEQ ID NO 29
<211> LENGTH: 53
<212> TYPE: PRT
<213> ORGANISM: Staphylococcus aureus

<400> SEQUENCE: 29

Leu Asp Gln Leu Pro Lys Asn Lys Ile Ser Thr Ala Lys Val Asp Ser
1               5                   10                  15

Thr Phe Ser Tyr Ser Ser Gly Gly Lys Phe Asp Ser Thr Lys Gly Ile
            20                  25                  30

Gly Arg Thr Ser Ser Asn Ser Tyr Ser Lys Thr Ile Ser Tyr Asn Gln
            35                  40                  45

Gln Asn Tyr Asp Thr
    50

<210> SEQ ID NO 30
<211> LENGTH: 8
<212> TYPE: PRT
<213> ORGANISM: Staphylococcus aureus

<400> SEQUENCE: 30

Lys Thr Asn Ile Leu Gln Asn Leu
1               5

<210> SEQ ID NO 31
<211> LENGTH: 57
<212> TYPE: DNA
<213> ORGANISM: Staphylococcus aureus

<400> SEQUENCE: 31
ggcggtacct acagtacctc tgacttcatc atggaggcta ctcgcactct gactgag     57
```

```
<210> SEQ ID NO 32
<211> LENGTH: 20
<212> TYPE: DNA
<213> ORGANISM: Staphylococcus aureus

<400> SEQUENCE: 32
cgggctttgt tagcagccgg                                                20

<210> SEQ ID NO 33
<211> LENGTH: 19
<212> TYPE: DNA
<213> ORGANISM: Staphylococcus aureus

<400> SEQUENCE: 33
ttcgctcgac ttgcatgta                                                 19

<210> SEQ ID NO 34
<211> LENGTH: 26
<212> TYPE: DNA
<213> ORGANISM: Staphylococcus aureus

<400> SEQUENCE: 34
gatgttgttt acgatagctt acatgc                                         26

<210> SEQ ID NO 35
<211> LENGTH: 19
<212> TYPE: DNA
<213> ORGANISM: Staphylococcus aureus

<400> SEQUENCE: 35
tgatcctggc tcaggatga                                                 19

<210> SEQ ID NO 36
<211> LENGTH: 17
<212> TYPE: DNA
<213> ORGANISM: Staphylococcus aureus

<400> SEQUENCE: 36
cgctggcggc gtgccta                                                   17

<210> SEQ ID NO 37
<211> LENGTH: 28
<212> TYPE: DNA
<213> ORGANISM: Staphylococcus aureus

<400> SEQUENCE: 37
aattagcaag tgagtaacat ttgctagt                                       28

<210> SEQ ID NO 38
<211> LENGTH: 38
<212> TYPE: DNA
<213> ORGANISM: Staphylococcus aureus

<400> SEQUENCE: 38
agttagtttc cttggactca gtgctatgta ttttttctt                           38
```

```
<210> SEQ ID NO 39
<211> LENGTH: 20
<212> TYPE: DNA
<213> ORGANISM: Staphylococcus aureus

<400> SEQUENCE: 39
cgggctttgt tagcagccgg                                               20
```

VLP-BASED VACCINES FOR TARGETING *STAPHYLOCOCCUS AUREUS* SECRETED VIRULENCE FACTORS

RELATED APPLICATIONS

This application is a United States national phase patent application claiming benefit of international patent application number PCT/US2017/015960 of international filing date 1 Feb. 2017, which claims the benefit of priority of United States provisional application U.S. 62/290,092 of identical title, filed Feb. 2, 2016, the entire contents of which said two applications is incorporated by reference herein.

GRANT SUPPORT

This invention was made with government support under grant nos. AI091917, AI114706 and AI083305 awarded by the National Institutes of Health. The government has certain rights in the invention.

FIELD OF THE INVENTION

The present invention is directed to virus-like particles (VLPs) which are engineered to present epitopes from *Staphylococcus aureus* (SA) autoinducing peptides (AIPs), which regulate quorum-sensing dependent virulence in this pathogen, or epitopes from SA toxins and leukocidins. These VLPs may be used to provide immunogenic compositions and efficacious vaccines. In a mouse model of SA dermonecrosis, vaccination with AIP-containing VLPs or SA toxin-containing VLPs induces protective immunity to limit the pathogenesis of SA infection and promote bacterial clearance.

BACKGROUND AND OVERVIEW OF THE INVENTION

The Gram Positive pathogen *Staphylococcus aureus* (SA), including both methicillin-sensitive and methicillin-resistant SA (MSSA, MRSA), is a major cause of human disease and the primary cause of skin and soft tissue infection (SSTI) in the US. *Staphylococcus aureus* is a Gram-positive bacterium well known for what is commonly known as staph infections. More serious forms of this infection can progress to bacterial pneumonia and bacteria in the bloodstream. These conditions sometimes can be fatal. With the advent of antibiotics, over time certain strains of *S. aureus* became resistant to antibiotics. Drug-resistant, including methicillin-resistant *S. aureus* (MRSA) infections began to appear. Today, MRSA is viewed as any strain of *S. aureus* that has developed resistance to β-lactams and other antibiotics, which include the penicillins, erythromycin, methicillin, dicloxacillin, nafcillin, oxacillin, the cephalosporins and others. Resistance does render MRSA infections far more difficult to treat with standard antibiotics. MRSA is a dangerous infection and poses serious health problems to the general public especially in hospitals, prisons, and nursing homes, but also in various community settings. People who are immunocompromised (for example, those with diabetes) or have immune systems that are weakened are at much greater risk of infection than the general public. MRSA causes a range of diseases from skin and wound infections to pneumonia and bloodstream infections that can cause sepsis and death.

Both community acquired MRSA (CA-MRSA) and hospital acquired MRSA (HA-MRSA) are resistant to traditional anti-staphylococcal β-lactam antibiotics.

*Staphylococcus aureus* is the leading cause of skin and soft tissue infections (SSTIs) in the United States. Mounting antibiotic resistance requires innovative treatments such as ones that inhibit *S. aureus* pathogenicity and support innate immune clearance. *S. aureus* coordinates virulence factor expression through the density-dependent accessory gene regulator (agr) operon via secretion of cyclic autoinducing peptides (AIPs). *S. aureus* lacking agr fails to cause dermonecrosis in mouse models of SSTI and is more readily cleared compared to agr positive isolates. Therefore, the inventors hypothesized that vaccination against *S. aureus* AIP could generate protective immunity against subsequent SSTI challenge. Because *S. aureus* AIPs are too small to stimulate a natural immune response (7-9 amino acids), the inventors engineered a virus-like-particle (PP7-VLPs) for surface presentation of a modified autoinducing peptide sequence (AIP1S). VLP-based vaccines allow multivalent presentation of target antigens and are highly immunogenic due to their repetitive, virus-like structure. As expected, vaccination with PP7-AIP1S induced AIP1-specific antibodies, and transcriptional analysis of skin from vaccinated and challenged mice showed that PP7-AIP1S vaccination limits agr-activation in vivo. Most importantly, in a challenge model of *S. aureus* SSTI, PP7-AIP1S vaccinated mice showed significantly reduced dermonecrosis and increased bacterial clearance compared to control vaccinated mice, demonstrating the efficacy of this vaccination approach. To the best of our knowledge, this is the first report of an efficacious, VLP-based vaccine which induces immune control of *S. aureus* AIP1-regulated virulence. To date, no vaccine against SA has been successful in clinical trials. However, these data suggest that VLP-based vaccination, in particular, PP7-AIP1S vaccination could be an effective tool to limit *S. aureus* pathogenesis during SSTI.

BRIEF DESCRIPTION OF THE INVENTION

Pursuant to the present invention, the inventors used VLPs to present epitopes from SA autoinducing peptides (AIPs), which regulate quorum-sensing dependent virulence in this pathogen, or epitopes from SA toxins and leukocidins, as efficacious vaccines. In a mouse model of SA dermonecrosis, vaccination with AIP-VLPs or SA toxin-VLPs induces protective immunity to limit the pathogenesis of SA infection and promote bacterial clearance.

The development and commercialization of vaccines for bacterial infections, especially vaccines for *Staphylococcus aureus* infections including MRSA, would be a significant public health breakthrough towards the goal of controlling and eradicating *Staphylococcus aureus* infections, especially MRSA infections, given how rapidly bacterial resistance occurs in these microbes.

The present invention provides immunotherapeutic and prophylactic bacteriophage viral-like particles (VLPs) which are useful in the treatment and prevention of *Staphylococcus aureus* (SA) infections, especially MRSA and related disorders. Related compositions (e.g. vaccines), nucleic acid constructs, and therapeutic methods are also provided. VLPs and related compositions of the invention induce high titer antibody responses against *Staphylococcus aureus* and protect against SA challenge in vivo. VLPs, VLP-containing compositions, and therapeutic methods of the invention induce an immunogenic response against SA infection, confer immunity against SA infection, protect against SA infection, and reduce the likelihood of infection by and/or inhibit SA infection, especially including MRSA infection.

Because antibodies that are specific for epitopes of AIPs which are thiolactone (cyclic), peptides may be necessary for antibody-mediated neutralization of *Staphylococcus aureus*. AIP1 or AIP1S (also referred to as AIP1C4S) targeting VLPs and related compositions (e.g. vaccines) of the invention provide a more comprehensive protection against infection by *Staphylococcus aureus*, especially including MRSA. Surprisingly, these do not require the presence of the thiolactone in the epitopic peptide in order to provide excellent immunogenicity.

Thus, the invention provides immunotherapeutic and prophylactic bacteriophage viral-like particle (VLPs) which are useful in the prevention of *Staphylococcus aureus* (SA), including MRSA, infections and related disease states and conditions, including persistent infections associated with SA. Related compositions (e.g. vaccines), nucleic acid constructs, and therapeutic methods are also provided. VLPs and related compositions of the invention induce high titer antibody responses against *S. aureus* and protect against *S. aureus* challenge in vivo. VLPs, VLP-containing compositions, and therapeutic methods of the invention induce an immunogenic response against SA infection, confer immunity against SA infection, protect against SA infection, and reduce the likelihood of infection by SA.

In a first embodiment, the invention provides a VLP comprising a bacteriophage single chain coat polypeptide dimer and an epitopic *S. aureus* heterologous peptide ("SA peptide"), wherein the epitopic SA peptide is displayed on the VLP in the A-B loop (in the downstream or upstream A-B loop, preferably the downstream A-B loop), or at the amino or carboxyl terminal ends of the dimer, and wherein vaccination with the VLP is prophylactic for *S. aureus*-induced disorders. In embodiments of the invention, the epitopic SA heterologous peptide is a SA autoinducing peptide (AIP), which regulates quorum-sensing dependent virulence in SA or is an epitopic peptide from SA toxins and lukocidins as otherwise described herein. In preferred embodiments, the epitopic SA heterologous peptide is the peptide AIP1 (YSTCDFIM, SEQ. ID NO: 1) or the peptide AIP1S (YSTSDFIM SEQ. ID NO:2), which are set forth in FIG. 10 hereof (note that the thiolactone is not expressed on the VLP). In preferred embodiments of the invention, the expressed epitopic peptide on the VLP does not contain a thiolactone group. In alternative preferred embodiments, the SA heterologous peptide is AIP2 GVNACSSLF (SEQ ID NO: 3) or AIP2S GVNASSSLF (SEQ ID NO: 4) AIP3 INCDFLL (SEQ ID NO: 5) or AIP3S INSDFLL (SEQ ID NO: 6) AIP4 YSTCYFIM (SEQ ID NO: 7) or AIP4S YSTSYFIM (SEQ ID NO: 8). In certain embodiments, the VLP expresses two of the above heterologous epitopic peptides.

In another aspect, the invention provides a composition comprising a VLP comprising a bacteriophage single chain coat polypeptide dimer and an epitopic SA peptide, wherein the epitopic SA peptide is displayed on the VLP, and wherein the composition is prophylactic for SA-induced disorders, especially including SA infections, including MRSA and related disease states and/or conditions.

Certain aspects of the invention reflect that the single-chain dimer of PP7 (as well as MS2) coat protein can tolerate the insertion of a wide variety of peptides, including peptides derived from cyclic autoinducing peptides AIPs and are highly immunogenic, even though the AIPs tend to be of small size and the thiolactone bond has heretofore hindered vaccine development.

In addition to heterologous peptides based upon AIPs, other SA toxin and leukocidin peptide sequences may be used and are described in greater detail in the detailed description of the invention which follows.

In another aspect, the invention provides a composition comprising a VLP comprising a bacteriophage single chain coat polypeptide dimer and a SA epitopic peptide as otherwise described herein (preferably, a AIP peptide, e.g. AIP1, AIP1S, AIP2, AIP2S, AIP3, AIP3S, AIP4 or AIP4S, especially AIP1 or AIP1S as otherwise described herein), wherein the heterologous peptide is displayed on the VLP, preferably in an unconstrained conformation, and preferably encapsidates bacteriophage mRNA, and wherein the composition is immunotherapeutic and prophylactic for SA-induced disorders. The AIP peptide, when incorporated into the VLP does not contain a thiolactone or is displayed without the thiolactone (the carboxylic acid of the methionine is incorporated as a peptide bond into the VLP structure), while still providing excellent immunogenicity.

In certain embodiments, VLPs and VLP-containing compositions (e.g. vaccines) of the invention are comprised of VLPs comprising AIP peptides, heterologous peptides from SA toxins and/or lukocidins. In other aspects, VLPs and VLP-containing compositions of the invention comprise hybrid VLPs that display SA epitopic peptide sequences preferably in an unconstrained conformation derived from several AIPs (e.g. AIP1, AIP1S, AIP2, AIP2S, AIP3, AIP3S, AIP4 or AIP4S).

In another aspect, the invention provides a composition comprising a VLP displaying SA epitopic peptides from two or more peptides on the same VLP, preferably in an unconstrained conformation, and wherein the composition is immunotherapeutic and prophylactic for SA-induced disorders.

In embodiments, the invention provides a VLP, or a composition comprising a VLP, wherein the VLP is made by transforming a prokaryote with a nucleic acid construct comprising either:

(1) (a) a bacterial or bacteriophage promoter which is operably associated with a coding sequence of a bacteriophage (e.g., PP7 or MS2, preferably a PP7) single chain coat polypeptide dimer, wherein the coat polypeptide dimer coding sequence is modified to: (i) define a first restriction site which is located in the upstream or downstream (preferably upstream) portion of the coat polypeptide dimer coding sequence and which is either positioned 5' to, or located within, the sequence which defines the coat polypeptide dimer A-B loop, N-terminus or carboxy-terminus, and (ii) contain a nucleotide sequence encoding a SA epitopic peptide; (b) a second restriction site positioned 3' to the coat polypeptide dimer coding sequence; (c) an antibiotic resistance gene which is operably associated with the promoter, and (d) a replication origin for replication in a prokaryotic cell; or (2) (a) a bacterial or bacteriophage promoter which is operably associated with a coding sequence of bacteriophage (e.g. PP7 or MS2 single chain coat polypeptide dimer, wherein the coat polypeptide dimer coding sequence is modified to (i) define a codon sequence positioned 5' to that portion of the sequence which defines the coat polypeptide dimer A-B loop, N-terminus or carboxy-terminus, and (ii) contain a nucleotide sequence encoding a SA epitopic peptide; (b) a restriction site positioned 3' to the coat polypeptide dimer coding sequence; (c) a PCR primer positioned 3' to the second restriction site; (d) a repressor to resistance to a first antibiotic, wherein the repressor is operably associated with the promoter; (e) a helper phage gene modified to contain a gene conferring resistance to a second antibiotic, and (f) a replication origin for replication in a prokaryotic cell.

In certain aspects, the invention provides a VLP, or a composition comprising a VLP, wherein the VLP is made by transforming a prokaryote with a nucleic acid construct comprising either:

(1) (a) a bacterial or bacteriophage promoter which is operably associated with a coding sequence of a bacteriophage (preferably PP7 or MS2, more preferably PP7) single chain coat polypeptide dimer, wherein the coat polypeptide dimer coding sequence is modified to: (i) define a first restriction site which is located in the downstream portion of the coat polypeptide dimer coding sequence and which is either positioned 5' to, or located within, the sequence which defines the coat polypeptide dimer AB loop, and (ii) contain a nucleotide sequence encoding a SA epitopic peptide, preferably a AIP epitopic peptide, such as AIP1 or AIP1S;
(b) a second restriction site positioned 3' to the coat polypeptide dimer coding sequence;
(c) an antibiotic resistance gene which is operably associated with the promoter; and
(d) a replication origin for replication in a prokaryotic cell; or
(2) (a) a bacterial or bacteriophage promoter which is operably associated with a coding sequence of a bacteriophage (preferably PP7 or MS2, more preferably PP7), single chain coat polypeptide dimer, wherein the coat polypeptide dimer coding sequence is modified to:
(i) define a first restriction site which is located in the downstream portion of the coat polypeptide dimer coding sequence and which is either positioned 5' to, or located within (preferably within), the sequence which defines the coat polypeptide dimer AB loop, and
(ii) contain a nucleotide sequence encoding a SA epitopic peptide, preferably a AIP epitopic peptide, such as AIP1 or AIP1S;
(b) a second restriction site positioned 3' to the coat polypeptide dimer coding sequence;
(c) a PCR primer positioned 3' to the second restriction site;
(d) an antibiotic resistance gene which is operably associated with the promoter; and
(e) a replication origin for replication in a prokaryotic cell; or
(3) (a) a bacterial or bacteriophage promoter which is operably associated with a coding sequence of a bacteriophage (preferably PP7 or MS2, more preferably PP7) single chain coat polypeptide dimer, wherein the coat polypeptide dimer coding sequence is modified to (i) define a codon sequence positioned 5' to that portion of the sequence which defines the coat polypeptide dimer AB loop, and (ii) contain a nucleotide sequence encoding a SA epitopic peptide, preferably a AIP epitopic peptide, such as AIP1 or AIP1S;
(b) a restriction site positioned 3' to the coat polypeptide dimer coding sequence;
(c) a PCR primer positioned 3' to the second restriction site;
(d) an antibiotic resistance gene for resistance to a first antibiotic, wherein the resistance gene is operably associated with the promoter;
(e) a helper phage gene modified to contain a second antibiotic resistance gene conferring resistance to a second antibiotic, and
(f) a replication origin for replication in a prokaryotic cell.

In alternative embodiments, the present invention provides a VLP, or a composition comprising a VLP, wherein the VLP is made by transforming a prokaryote with a nucleic acid construct comprising either:

(1) (a) a bacterial or bacteriophage promoter which is operably associated with a coding sequence of bacteriophage PP7 single chain coat polypeptide dimer, wherein the coat polypeptide dimer coding sequence is modified to: (i) define a first restriction site which is located in the downstream portion of the coat polypeptide dimer coding sequence and which is either positioned 5' to, or located within, the sequence which defines the coat polypeptide dimer N-terminus, and (ii) contain a nucleotide sequence encoding a SA epitopic peptide, preferably a AIP epitopic peptide, such as AIP1 or AIP1S; (b) a second restriction site positioned 3' to the coat polypeptide dimer coding sequence; (c) an antibiotic resistance gene which is operably associated with the promoter, and (d) a replication origin for replication in a prokaryotic cell; or
(2) (a) a bacterial or bacteriophage promoter which is operably associated with a coding sequence of bacteriophage MS2 single chain coat polypeptide dimer, wherein the coat polypeptide dimer coding sequence is modified to (i) define a codon sequence positioned 5' to that portion of the sequence which defines the coat polypeptide dimer N-terminus, and (ii) contain a nucleotide sequence encoding a SA epitopic peptide, preferably a AIP epitopic peptide, such as AIP1 or AIP1S; (b) a restriction site positioned 3' to the coat polypeptide dimer coding sequence; (c) a PCR primer positioned 3' to the second restriction site; (d) a repressor to resistance to a first antibiotic, wherein the repressor is operably associated with the promoter; (e) a helper phage gene modified to contain a gene conferring resistance to a second antibiotic, and (f) a replication origin for replication in a prokaryotic cell.

In certain aspects, the invention provides VLPs made by transforming a prokaryote with a SA epitopic peptide sequence-containing construct as described herein. In other aspects, VLPs and VLP-containing compositions (e.g. vaccines) of the invention are comprised of VLPs comprising SA epitopic peptides derived from SA autoinducing peptides, which regulate quorum-sensing dependent virulence in SA or epitopic peptides from SA toxins and lukocidins. In other aspects, VLPs and VLP-containing compositions of the invention comprise hybrid VLPs that display multiple SA epitopic sequences.

In certain embodiments, the coding sequence of the bacteriophage single chain coat polypeptide dimer, especially PP7 or MS2, preferably PP7, further comprises a transcription terminator positioned 5' to the second restriction site.

In certain aspects, the invention provides a method of inoculating a subject at risk of developing a SA-related disorder, including an SA infection, including a MRSA infection, the method comprising administering to the subject one or more doses of a composition comprising a SA epitopic peptide-containing VLP as described herein. In other aspects, the invention provides a method of treating a subject who is at risk of developing a SA-related infection, including MRSA or a disorder, the method comprising administering to the subject one or more doses of a composition comprising a SA epitopic peptide-containing VLP as described herein. In still other aspects, the invention provides a method of treating a subject who has developed a SA-related infection or disorder, including MRSA, the method comprising administering to the subject one or more doses of a composition comprising a SA epitopic peptide containing VLP as described herein.

Thus, the inventors describe the use of recombinant VLPs derived RNA bacteriophages to induce high titer antibody responses against SA epitopic peptides that protect against SA infections, including MRSA infections and related disorders.

These and other aspects of the invention are described further in the Detailed Description of the Invention, which follows.

BRIEF DESCRIPTION OF THE FIGURES

FIG. 1 shows the cloning of the *Staphylococcus aureus* (SA) autoinducing peptide 1 (AIP1) with a C4S mutation into the AB loop of the PP7 dimer. This peptide is also referred to as AIP1S. AIP1 is the quorum sensing peptide produced by agr type I SA isolates and is required for agr signaling and virulence. SA isolates exist as one of four agr types (agr I-IV) with each type making a corresponding AIP (AIP1-4).

FIG. 11 PP7-AIP1S vaccination induces antibodies which recognize soluble AIP1. BALB/c mice were vaccinated twice (i.m.) at 4 week intervals with 10 μg of PP7-AIP1S or PP7 wild-type (control). (a) Serum was collected at the indicated time points after the second vaccination. Serum was then pooled (n=3 mice per group), treated as described in Materials and Methods, and relative binding to PP7-AIP1S determined by ELISA. (b) PP7-AIP1S antiserum collected at eight weeks after the second vaccination was prepared as in (a), and relative AIP1S binding determined in the presence and absence of the indicated concentrations of AIP1 or AIP2 (n=3 mice per group; duplicate experiments performed in triplicate). Data are mean±s.e.m. Kruskal-Wallis ANOVA $p<0.0001$ with Dunn's post-test: *$p<0.05$; ***$p<0.001$.

DETAILED DESCRIPTION OF THE INVENTION

Figure 2:
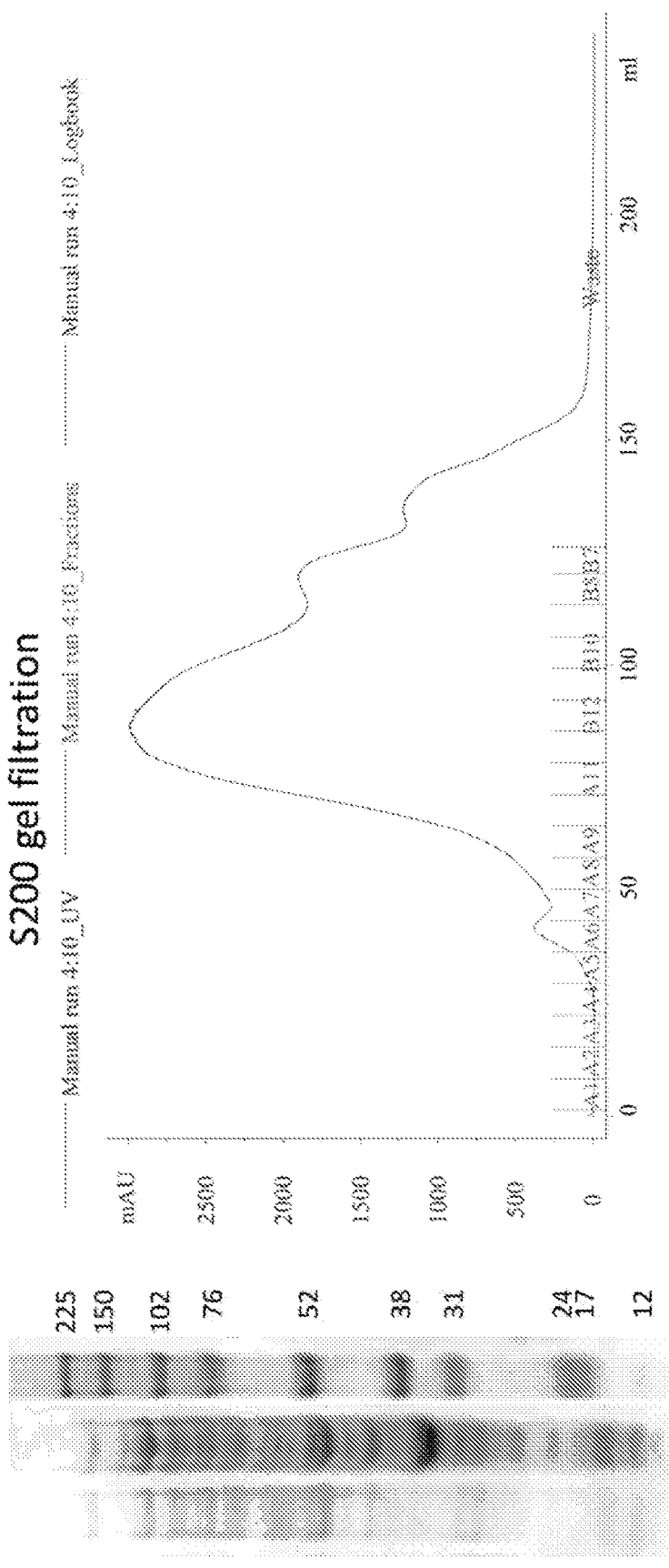
FIG. 2 shows purification of PP7-AIP1S on gel filtration (right).

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes 1-III; Coligan, ed., 1994, "Current Protocols in Immunology" Volumes 1-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal and preferably a human, to whom treatment, including prophylactic treatment (prophylaxis), with the immunogenic compositions and/or vaccines according to the present invention is provided. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe a number of VLP's or an amount of a VLP-containing composition which, in context, is used to produce or effect an intended result, whether that result relates to the prophylaxis and/or therapy of an SA-induced or SA-related disorder or disease state, including an SA infection or as otherwise described herein. The term effective subsumes all other effective amount or effective concentration terms (including the term "therapeutically effective") which are otherwise described or used in the present application.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

The term "single-chain dimer" refers to a normally dimeric protein whose two subunits of coat polypeptide of a RNA bacteriophage have been genetically (chemically, through covalent bonds) fused into a single polypeptide chain. Specifically, in the present invention single-chain dimer versions of PP7 coat proteins were constructed. Each of these proteins is naturally a dimer of identical polypeptide chains. In the PP7 coat protein dimers the N-terminus of one subunit lies in close physical proximity to the C-terminus of the companion subunit. Single-chain coat protein dimers were produced using recombinant DNA methods by duplicating the DNA coding sequence of the coat proteins and then fusing them to one another in tail to head fashion. The result is a single polypeptide chain in which the coat protein amino acid appears twice, with the C-terminus of the upstream copy covalently fused to the N-terminus of the downstream copy. Normally (wild-type) the two subunits are associated only through noncovalent interactions between the two chains. In the single-chain dimer these noncovalent interactions are maintained, but the two subunits have additionally been covalently tethered to one another. This greatly stabilizes the folded structure of the protein and confers to it its high tolerance of peptide insertions as described above.

This application makes frequent reference to coat protein's "AB-loop". The RNA phage coat proteins possess a conserved tertiary structure. The PP7 coat proteins, for example, possess a structure wherein each of the polypeptide chains is folded into of a number of β-strands. The β-strands A and B form a hairpin with a three-amino acid loop connecting the two strands at the top of the hairpin, where it is exposed on the surface of the VLP. As evidenced in the present application, peptides inserted into the AB-loop are exposed on the surface of the VLP and are strongly immunogenic.

The amino acid residues described herein are preferred to be in the "L" isomeric form. However, residues in the "D" isomeric form can be substituted for any L-amino acid residue, as long as the desired functional is retained by the polypeptide. $NH_2$ refers to the free amino group present at the amino terminus of a polypeptide. COOH refers to the free carboxy group present at the carboxy terminus of a polypeptide.

The term "valency" is used to describe the density of the SA epitopic peptide (preferably a heterologous AIP thiolactone peptide such as AIP1 or AIPS) displayed on VLPs according to the present invention. Valency in the present invention may range from low valency to high valency, from less than 1 to more than about 180, preferably 90 to 180. Immunogenic compositions according to the present invention comprise VLPs which are preferably high valency and comprise VLPs which display at least 50-60 up to about 180 or more SA epitopic peptides, preferably an AIP, more preferably AIP1 or AIPS.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

A "heterologous" region of a recombinant cell is an identifiable segment of nucleic acid within a larger nucleic acid molecule that is not found in association with the larger molecule in nature.

An "origin of replication" refers to those DNA sequences that participate in DNA synthesis.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

In bacteria, transcription normally terminates at specific transcription termination sequences, which typically are categorized as rho-dependent and rho-independent (or intrinsic) terminators, depending on whether they require the action of the bacterial rho-factor for their activity. These terminators specify the sites at which RNA polymerase is caused to stop its transcription activity, and thus they largely define the 3'-ends of the RNAs, although sometimes subsequent action of ribonucleases further trims the RNA.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional and translational control sequences are DNA regulatory sequences, such as promoters, enhancers, polyadenylation signals, terminators, and the like, that provide for the expression of a coding sequence in a host cell.

An "antibiotic resistance gene" refers to a gene that encodes a protein that renders a bacterium resistant to a given antibiotic. For example, the kanamycin resistance gene directs the synthesis of a phosphotransferase that modifies and inactivates the drug. The presence on plasmids of a kanamycin resistance gene provides a mechanism to select for the presence of the plasmid within transformed bacteria. Similarly, the chloramphenicol resistance gene allows bacteria to grow in the presence of the drug by producing an acetyltransferase enzyme that inactivates the antibiotic through acetylation.

The term "PCR" refers to the polymerase chain reaction, a technique used for the amplification of specific DNA sequences in vitro. The term "PCR primer" refers to DNA sequences (usually synthetic oligonucleotides) able to anneal to a target DNA, thus allowing a DNA polymerase (e.g. Taq DNA polymerase) to initiate DNA synthesis. Pairs of PCR primers are used in the polymerase chain reaction to initiate DNA synthesis on each of the two strands of a DNA and to thus amplify the DNA segment between two primers. Representative PCR primers which used in the present invention are those which are presented in the examples section hereof. Additional PCR primers may be obtained for the various SA epitopic peptides which are presented herein.

Examples of primers used for PCR described above and otherwise in the present invention are presented in the examples section (Methods). In addition to those primers, the following primer E3.2: 5' CGG GCT TTG TTA GCA GCC GG 3'—(SEQ ID No. 39) may serve as the 3' (reverse)-primer in PCR reactions to amplify coat protein. Primers useful in the present invention, among others, are otherwise set forth in the examples (Methods) section of the present application.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid, which normally replicate independently of the bacterial chromosome by virtue of the presence on the plasmid of a replication origin. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

As used herein, "epitope" refers to an antigenic determinant of a polypeptide. An epitope could comprise 3 amino acids in a spatial conformation which is unique to the epitope. Generally an epitope consists of at least 4 such amino acids, and more often, consists of at least 5-10 such amino acids. Methods of determining the spatial conformation of amino acids are known in the art, and include, for example, x-ray crystallography and 2-dimensional nuclear magnetic resonance.

As used herein, the term "coat protein(s)" refers to the protein(s) of a bacteriophage or a RNA-phage capable of being incorporated within the capsid assembly of the bacteriophage or the RNA-phage. These include, but are not limited to PP7, MS2, AP205, Qβ, R17, SP, PP7, GA, M11, MX1, f4, Cb5, Cb12r, Cb23r, 7s and f2 RNA bacteriophages. Preferred coat proteins which are used in the present invention include coat proteins from bacteriophages include PP7, MS2, AP205, Qβ. Preferably, PP7 or MS2 coat polypeptides are used to create VLPs according to the present invention.

As used herein, a "coat polypeptide" as defined herein is a polypeptide fragment of the coat protein that possesses coat protein function and additionally encompasses the full length coat protein as well or single-chain variants thereof.

As used herein, the term "immune response" refers to a humoral immune response and/or cellular immune response leading to the activation or proliferation of B- and/or T-lymphocytes and/or antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response as described above, whether alone or linked to a carrier in the presence or absence of an adjuvant. Preferably, antigen presenting cell may be activated.

As used herein, the term "vaccine" refers to a formulation which contains the composition of the present invention and which is in a form that is capable of being administered to an animal, often a human patient or subject.

As used herein, the term "virus-like particle of a bacteriophage" refers to a virus-like particle (VLP) resembling the structure of a bacteriophage, being non-replicative and noninfectious, and lacking at least the gene or genes encoding for the replication machinery of the bacteriophage, and typically also lacking the gene or genes encoding the protein or proteins responsible for viral attachment to or entry into the host.

This definition should, however, also encompass viruslike particles of bacteriophages, in which the aforementioned gene or genes are still present but inactive, and, therefore, also leading to non-replicative and noninfectious virus-like particles of a bacteriophage.

VLP of RNA bacteriophage coat protein: The capsid structure formed from the self-assembly of one or more subunits of RNA bacteriophage coat protein and optionally containing host RNA is referred to as a "VLP of RNA bacteriophage coat protein". In a particular embodiment, the capsid structure is formed from the self assembly of 90 coat protein single-chain dimers or 180 coat protein monomers.

A nucleic acid molecule is "operatively linked" to, or "operably associated with", an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

SA-Induced Disorders, immunogenicity, and Prophylactic Efficacy

"SA-induced disorders" or "SA-related disorders" include, but are not limited to, the disorders identified in this application which are caused by *S. aureus* infections, including the infection itself, which may be a methicillin sensitive *Staphylococcus aureus* (MSSA) infection or a methicillin resistant *Staphylococcus aureus* (MRSA) infection. Immunogenicity and prophylactic efficacy (e.g. whether a composition is prophylactic for SA-induced disorders) may be evaluated either by the techniques and standards mentioned in this section, or through other methodologies that are well-known to those of ordinary skill in the art.

To assess immunogenicity (e.g. whether a composition has induced a high titer antibody responses against SA), an anti-SA geometric mean titer (GMT) can be Measured by ELISA, e.g. after a few weeks of treatment (e.g. 3 or 4 weeks) and after administration of a few dosages (e.g. 3 or 4). The percentage of subjects who seroconverted for SA after a few weeks of treatment (e.g. 3 or 4 weeks) and after administration of a few dosages (e.g. 3 or 4) can also be determined to assess immunogenicity.

To determine prophylactic efficacy, an immunogenicity analysis can be conducted on subjects who remain SA seronegative and PCR-negative to SA infection (swab and biopsy) at various endpoints after challenge.

*Staphylococcus aureus*

"SA epitopic peptide" as used herein includes the *S. aureus* epitopic peptides of all autoinducing peptides (AIPs), which regulate quorum-sensing dependent virulence in this pathogen, or epitopes from SA toxins and leukocidins. These epitopic peptides include the following, which can be inserted into VLPs in the A-B loop (upstream or downstream, preferably in the downstream A-B loop) or in the amino or carboxyl terminus of a bacteriophage protein coat dimer.

Production of Virus-Like Particles

The present invention is directed to virus-like phage particles as well as methods for producing these particles in vivo as well as in vitro. As used herein, producing virions "in vitro" refers to producing virions outside of a cell, for instance, in a cell-free system, while producing virions "in vivo" refers to producing virions inside a cell, for instance, an *Escherichia coli* or *Pseudomonas aeruginosa* cell.

Bacteriophages

The VLPs described here consist of assemblies of the coat proteins of single-strand RNA bacteriophage [RNA Bacteriophages, in The Bacteriophages. Calendar, R L, ed. Oxford University Press. 2005]. The known viruses of this group attack bacteria as diverse as *E. coli, Pseudomonas* and *Acinetobacter*. Each possesses a highly similar genome organization, replication strategy, and virion structure. In particular, the bacteriophages contain a single-stranded (+)-sense RNA genome, contain maturase, coat and replicase genes, and have small (<300 angstrom) icosahedral capsids. These include but are not limited to PP7, MS2, AP205, Qβ, R17, SP, PP7, GA, M11, MX1, f4, Cb5, Cb12r, Cb23r, 7s and f2 RNA bacteriophages.

The information required for assembly of the icosahedral capsid shell of this family of bacteriophage is contained entirely within coat protein itself. For example, purified coat protein can form capsids in vitro in a process stimulated by the presence of RNA [Beckett et al., 1988, J. Mol Biol 204: 939-47]. Moreover, coat protein expressed in cells from a plasmid assembles into a virus-like particle in vivo [Peabody, D. S., 1990, J Biol Chem 265: 5684-5689].

Examples of PP7 coat polypeptides include but are not limited to the various chains of PP7 Coat Protein Dimer in Complex With Rna Hairpin (e.g. Genbank Accession Nos.

2QUXR; 2QUXO; 2QUX_L; 2QUX_I; 2QUX_F; and 2QUX_C). See also Example 1 herein and Peabody, et al., RNA recognition site of PP7 coat protein, Nucleic Acids Research, 2002, Vol. 30, No. 19 4138-4144.

RNA Bacteriophage Coat Polypeptide

The coat polypeptides useful in the present invention also include those having similarity with one or more of the coat polypeptide sequences disclosed above. The similarity is referred to as structural similarity. Structural similarity may be determined by aligning the residues of the two amino acid sequences (i.e., a candidate amino acid sequence and the amino acid sequence) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence can be isolated from a single stranded RNA virus, or can be produced using recombinant techniques, or chemically or enzymatically synthesized. Preferably, two amino acid sequences are compared using the BESTFIT algorithm in the GCG package (version 10.2, Madison Wis.), or the Blastp program of the BLAST 2 search algorithm, as described by Tatusova, et al. (*FEMS Microbial Lett* 1999, 174:247-250), and available at http://www.ncbi.nlm.nih.gov/blast/bl2seq/bl2.html. Preferably, the default values for all BLAST 2 search parameters are used, including matrix=BLOSUM62; open gap penalty=11, extension gap penalty=1, gap xdropoff=50, expect=10, word-size=3, and optionally, filter on. In the comparison of two amino acid sequences using the BLAST search algorithm, structural similarity is referred to as "identities." Preferably, a coat polypeptide also includes polypeptides with an amino acid sequence having at least 80% amino acid identity, at least 85% amino acid identity, at least 90% amino acid identity, or at least 95% amino acid identity to one or more of the amino acid sequences disclosed above. Preferably, a coat polypeptide is active. Whether a coat polypeptide is active can be determined by evaluating the ability of the polypeptide to form a capsid and package a single stranded RNA molecule. Such an evaluation can be done using an in vivo or in vitro system, and such methods are known in the art and routine. Alternatively, a polypeptide may be considered to be structurally similar if it has similar three-dimensional structure as the recited coat polypeptide and/or functional activity.

The SA Epitopic Peptide

As described herein, the SA epitopic peptide sequence may be present in the A-B loop, at the N-terminus or the carboxy terminus of a coat polypeptide, but preferably in the A-B loop in the downstream. Preferably, the SA epitopic peptide sequence is expressed on the outer surface of the capsid.

The SA epitopic peptide sequence includes but is not limited to amino acid sequences derived from the autoinducing peptides (AIPs), which regulate quorum-sensing dependent virulence in this pathogen, or epitopes from SA toxins and leukocidins.

In preferred embodiments, the present invention is directed to A-B loop, N-terminal or C-terminal presentation of SA AIP1-4 wild-type and C4S mutants epitopic SA peptides on VLPs including PP7, MS2, AP205 and Qβ. These VLP-AIPs can be used singly or as a combination vaccine. The inventors have generated preliminary data showing protection against infection using a vaccine consisting of a peptide from the SA toxin alpha-hemolysin (Hla) presented on AP205. Sequence alignment of Hla with SA bicomponent leukotoxins (including LukSF components of gamma hemolysin, Panton-Valentine leukocidin (PVL), Luk ED and LukGH) show similar peptide epitopes which are predicted to also induce neutralizing immunity, with the greatest protection provided by vaccination with a combined VLP-leukocidin cocktail.

Epitopic peptides which are used in the present invention include the following: In each instance of a peptide, at least four (4) contiguous amino acids are used as the epitopic peptide and anywhere from 4-9 contiguous amino acids (depending on the epitopic peptide employed).

```
AIP1
                                        (SEQ ID NO: 1)
YSTCDFIM
or

AIP1S
                                        (SEQ ID NO: 2)
YSTSDFIM

AIP2
                                        (SEQ ID NO: 3)
GVNACSSLF
or

AIP2S
                                        (SEQ ID NO: 4)
GVNASSSLF

AIP3
                                        (SEQ ID NO: 5)
INCDFLL
or

AIP3S
                                        (SEQ ID NO: 6)
INSDFLL

AIP4
                                        (SEQ IS NO: 7)
YSTCYFIM
or

AIP4S
                                        (SEQ ID NO: 8)
YSTSYFIM
```

Or truncations of any of the above (i.e. any 4, 5, 6, 7, 8 or 9 contiguous amino acids found within the sequences described above).

Additional SA epitopic peptides (or truncations as described herein below) include the following:

```
PVL (Panton-Valentine leukocidin
From LukS-PV Q2FGU9
1)
                                        (SEQ ID NO: 9)
INYLPKNKIDSVNVSQTLGYNIGGNFNSGPSTGGNGSFNYSKTTISYN
QQNYIS 2)
                                        (SEQ ID NO: 10)
KWGVTQNI From LukF-PV Q2FGV0
1)
                                        (SEQ ID NO: 11)
VDYAPKNQNEEFQVQQTVGYSYGGDINISNGLSGGGNGSKSFSETINYQ
ESYRT
```

-continued

2)

(SEQ ID NO: 12)
LKISQIL

From H1a-alpha hemolysin P09616
1)
(SEQ ID NO: 13)

STLTYGFNGNVTGDDTGKIGGLIGANVSIGHTLK

2)

(SEQ ID NO: 14)

ENGMHKKV

3)

(SEQ ID NO: 15)

SDYYPRNSIDKEY

4)

(SEQ ID NO: 16)

KYVQPDFKF

H1g-gamma-hemolysin

From A subunit P0A074
1)
(SEQ ID NO: 17)
INYLPKNKIDSADVSQKLGYNIGGNFQSAPSIGGSGSFNYSKTISYNQK
NYVT

2)

(SEQ ID NO: 18)

RLAITQNI

From B subunit P0A077

1)
(SEQ ID NO: 19)
VDYAPKNQNEEFQVQNTLGYTFGGDISISNGLSGGLNGNTAFSETINYKQ
ESYRT

2)

(SEQ ID NO: 20)

FKISQIL

1)

(SEQ ID NO: 21)
INYLPKNKIESTNVSQTLGYNIGGNFQSAPSLGGNGSFNYSKSISYTQQ
NYVS

2)

(SEQ ID NO: 22)

KWGVTQNI

LukED-

From Luk E Q2FXB0
1)
(SEQ ID NO: 23)
INYLPKNKIETTDVGQTLGYNIGGNFFQSAPSIGGNGSFNYSKTISYTQK
SYVS

2)

(SEQ ID NO: 24)

KWGVTQNV

From Luk D O54082

1)
(SEQ ID NO: 25)
VDYAPKNQNEEFQVQQTLGYSYGGDINISNGLSGGLNGSKSFSETINYKQ
ESYRT

2)

(SEQ ID NO: 26)

LNIFQIL

LukAB (also called LukGH)

From LukA/G sequence taken from SAUSA300_1974
1)
(SEQ ID NO: 27)
TDFAPKNQDESREVKYTYGYKTGGDFSINRGGLTGNITKESNYSETISYQ
QPSYRT

-continued

2)

(SEQ ID NO: 28)

KNITQSL

From LukB/H sequence taken from SAUSA300_1975

1)
(SEQ ID NO: 29)
LDQLPKNKISTAKVDSTFSYSSGGKFDSTKGIGRTSSNSYSKTISYNOQ
NYDT

2)

(SEQ ID NO: 30)

KTNILQNL

LukF, P31715

LukS, P31716

Or epitopic truncations of any of the above sequences (i.e. any 4, 5, 6, 7, 8, 9, 10, 11, 12, 13, 14, 15, 16, 17, 18, 19, 20, 21, 22, 23, 24, 25 up to 35 contiguous epitopic amino acids, where relevant or any epitopic amino acid sequence from any of the above amino acid sequences thereof comprising at least 4 contiguous amino acids).

In order to determine a corresponding position in a structurally similar coat polypeptide, the amino acid sequence of this structurally similar coat polypeptide is aligned with the sequence of the named coat polypeptide as specified above.

In a particular embodiment, the coat polypeptide is a single-chain dimer containing an upstream and downstream subunit. Each subunit contains a functional coat polypeptide sequence. The SA epitopic peptide sequence may be inserted in the upstream and/or downstream subunit at the sites mentioned herein above, e.g., the A-B loop, the N-terminus or a carboxyl terminus. In a particular embodiment, the coat polypeptide is a single chain dimer of a PP7 or MS2 coat polypeptide, preferably a PP7 coat polypeptide, although a number of bacteriophage coat polypeptides may be used.

Preparation of Transcription Unit

The transcription unit of the present invention comprises an expression regulatory region, (e.g., a promoter), a sequence encoding a coat polypeptide and transcription terminator. The RNA polynucleotide may optionally include a coat recognition site (also referred to a “packaging signal”, “translational operator sequence”, “coat recognition site”). Alternatively, the transcription unit may be free of the translational operator sequence. The promoter, coding region, transcription terminator, and, when present, the coat recognition site, are generally operably linked. “Operably linked” or “operably associated with” refer to a juxtaposition wherein the components so described are in a relationship permitting them to function in their intended manner. A regulatory sequence is “operably linked” to, or “operably associated with”, a coding region when it is joined in such a way that expression of the coding region is achieved under conditions compatible with the regulatory sequence. The coat recognition site, when present, may be at any location within the RNA polynucleotide provided it functions in the intended manner.

The invention is not limited by the use of any particular promoter, and a wide variety of promoters are known. The promoter used in the invention can be a constitutive or an inducible promoter. Preferred promoters are able to drive high levels of RNA encoded by me coding region encoding the coat polypeptide Examples of such promoters are known in the art and include, for instance, the lac promoter, T7, T3, and SP6 promoters.

The nucleotide sequences of the coding regions encoding coat polypeptides described herein are readily determined. These classes of nucleotide sequences are large but finite, and the nucleotide sequence of each member of the class can be readily determined by one skilled in the art by reference to the standard genetic code. Furthermore, the coding sequence of an RNA bacteriophage single chain coat polypeptide comprises a site for insertion of SA epitopic peptide-encoding sequences. In a particular embodiment, the site for insertion of the SA epitopic peptide-encoding sequence is a restriction enzyme site. In another embodiment, the SA epitopic peptide-encoding sequence is inserted using polymerase chain reaction (PCR) using standard techniques.

In a particular embodiment, the coding region encodes a single-chain dimer of the coat polypeptide. In a most particular embodiment, the coding region encodes a modified single chain coat polypeptide dimer, where the modification comprises an insertion of a coding sequence at least four amino acids at the insertion site, which four amino acids represent an epitopic SA peptide as otherwise described herein. The transcription unit may contain a bacterial promoter, such as a lac promoter or it may contain a bacteriophage promoter, such as a T7 promoter.

Synthesis

The VLPs of the present invention may be produced in vivo by introducing transcription units into bacteria, especially if transcription units contain a bacterial promoter. Alternatively, it may be synthesized in vitro in a coupled cell-free transcription/translation system.

Assembly of VLPs Encapsidating Heterologous Substances

As noted above, the VLPs of the present invention encapsidate a SA epitopic peptide-encoding sequence. These VLPs may be also be assembled in combination with another substance, such as an adjuvant. Specifically, purified coat protein subunits are obtained from VLPs that have been disaggregated with a denaturant (usually acetic acid). The adjuvant is mixed with coat protein, which is then reassembled in its presence. In a particular embodiment, the substance has some affinity for the interior of the VLP and is preferably negatively charged.

In another embodiment, the adjuvant is passively diffused into the VLP through pores that naturally exist in the VLP surface. In a particular embodiment, the substance is small enough to pass through these pores and has a high affinity for the interior of the VLP.

The following experiments were conducted to determine the potential for providing immunogenic VLPs which incorporate heterologous peptides from Staphylococcus aureus as potential compositions for inducing protection against Staphylococcus aureus infection, especially including MRSA infection.

Figure 9:
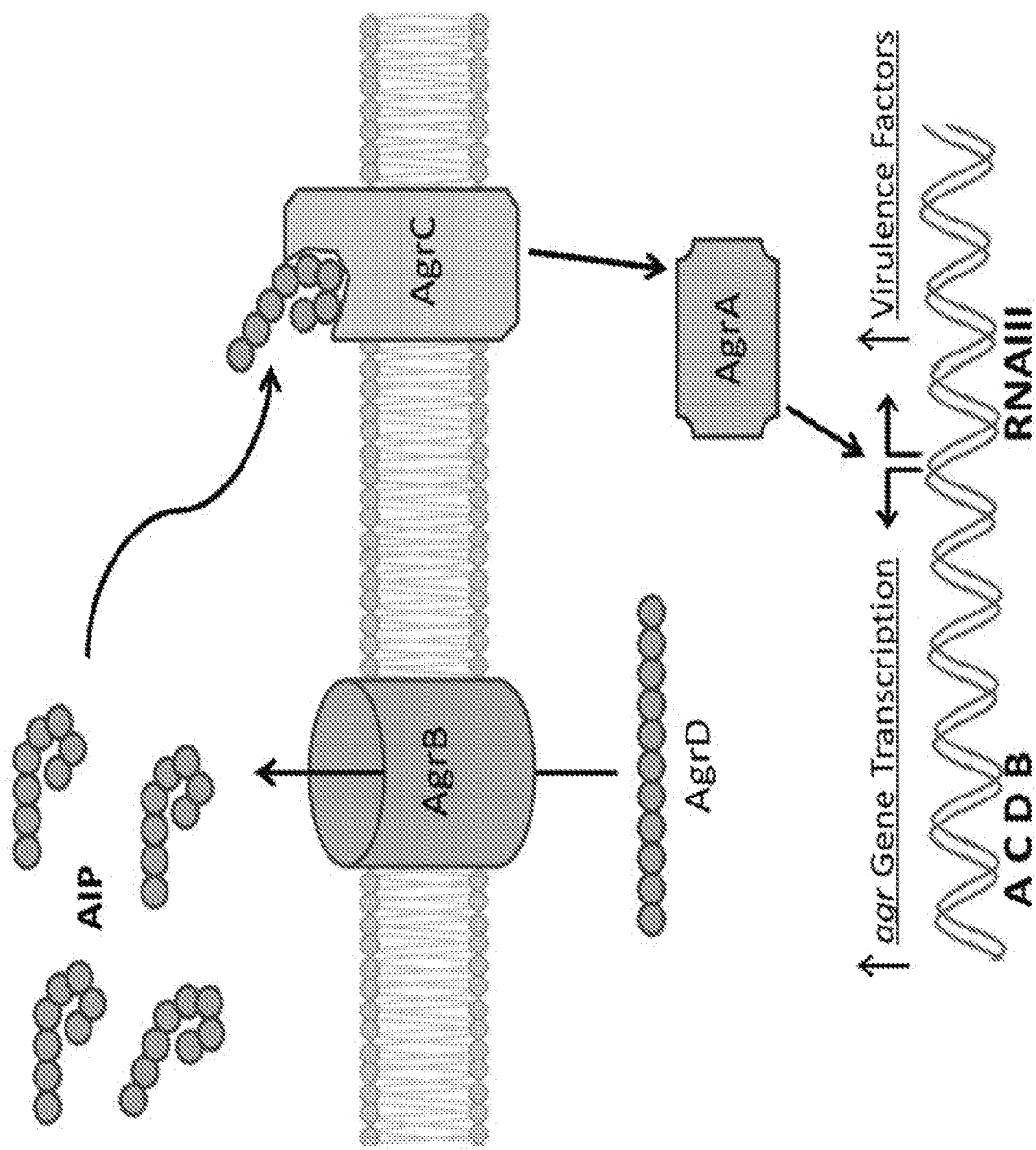
FIG. 9 shows the agr pathway schematic.

The following facts formed the basis of the rationale for the present invention:

Antibiotic resistance of Staphylococcus aureus emphasizes the importance of alternative approaches;

The S. aureus accessory gene regulator (agr) pathway utilizes secreted autoinducing peptides (AIPs) for virulence regulation. See FIG. 9, which shows the agr pathway.

AIPs (7-9 amino acids) are too small to invoke natural immune response, but might be effective targets if presented on Virus-like-particles (VLPs) which are natural adjuvants and can serve as effective vaccines.

Thus, the hypothesis emerged that vaccination with VLP-AIP will induce antibodies with structural recognition of native AIP, and thereby will confer immune protection from Staphylococcus aureus SSTI via agr disruption. The following examples test that hypothesis.

EXAMPLES

In certain preferred embodiments, the present invention is directed to A-B loop, N-terminal or C-terminal (preferably A-B loop) presentation of SA AIP1-4 wild-type and C4S mutant epitopic SA peptides on VLPs including PP7, MS2, AP205 and Qβ. These VLP-AIPs can be used singly or as a combination vaccine. The inventors have generated data showing protection against infection using a vaccine consisting of a peptide from the SA toxin alpha-hemolysin (Hla) presented on AP205. Sequence alignment of Hla with SA bicomponent leukotoxins (including LukSF components of gamma hemolysin, Panton-Valentine leukocidin (PVL), Luk ED and LukGH) show similar peptide epitopes which the inventors have predicted would also induce neutralizing immunity, with the greatest protection provided by vaccination with a combined VLP-leukocidin cocktail. With the expectation of immunogenic activity, further testing will concentrate on these embodiments, as well as others.

ADDITIONAL EXAMPLES

The production of virulence factors required for S. aureus SSTI is largely regulated by the accessory gene regulator operon (agr)[7,8] through a bacterial communication system known as quorum sensing. Induction of agr signaling depends upon the accumulation of small, secreted autoinducing peptides (AIPs) to activate a receptor histidine kinase, AgrC, in the bacterial cell membrane[9,10]. AgrC activation drives downstream production of the effector molecule, RNAIII, which in turn regulates expression of over 200 virulence genes contributing to invasive infection[7]. S. aureus isolates express one of four agr alleles (agr-I to agr-IV), with each secreting a unique AIP (AIP1-AIP4) and expressing a corresponding AgrC. Previously, both an anti-AIP4 monoclonal antibody (mAb)[11,12] and an AIP4 immunologic mimotope vaccine[13] showed protection against infection caused by agr type IV isolates. However, antibody or vaccine targeting of signaling by agr type I isolates, which are most associated with invasive S. aureus infection[14,15], has not been reported.

Figure 10:
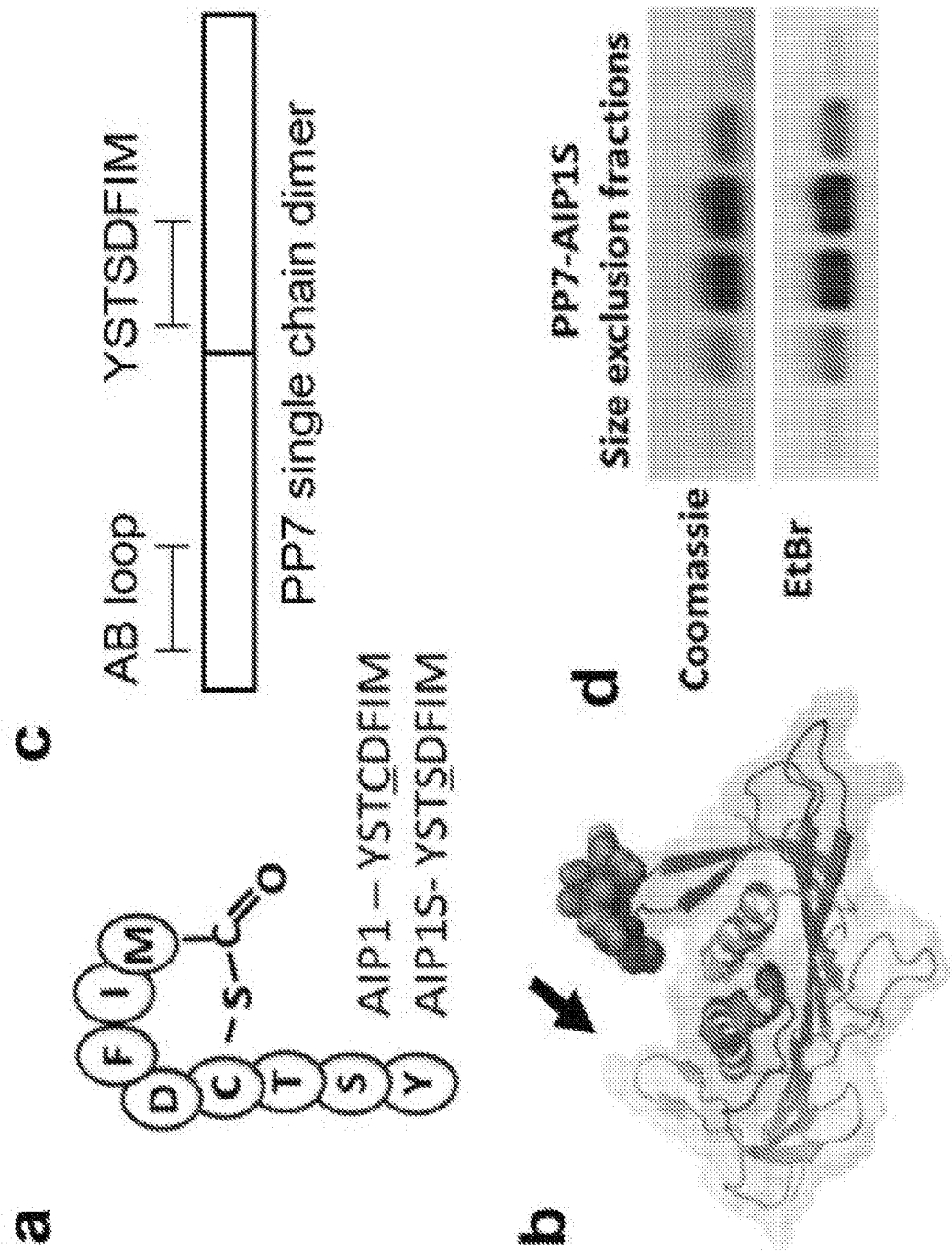
FIG. 10 shows the design and preparation of PP7-AIP1S VLPs. (a) Schematic of AIP1 and amino acid sequence of AIP1-C4S (AIP1 S). (b) Ribbon representation of the PP7 coat protein dimer depicting the first AB loop (indicated by arrow) and the AIP1 S sequence (spheres) modeled into the second AB loop (PDB ID 2QUD$_{21}$) using GalaxyWeb$_{31}$. Image prepared using PyMol (PyMOL molecular graphics system, version 1.5.0.4; Schrodinger, LLC). (c) Schematic of the site of AIP1S insertion into the second AB loop of the PP7 single chain dimer. (d) Agarose gel electrophoresis of size exclusion chromatography fractions showing assembly and purity of PP7-AIP1S based on Coomassie (protein) and ethidium bromide (EtBr) staining (showing VLP encapsulated nucleic acids).
Figure 12:
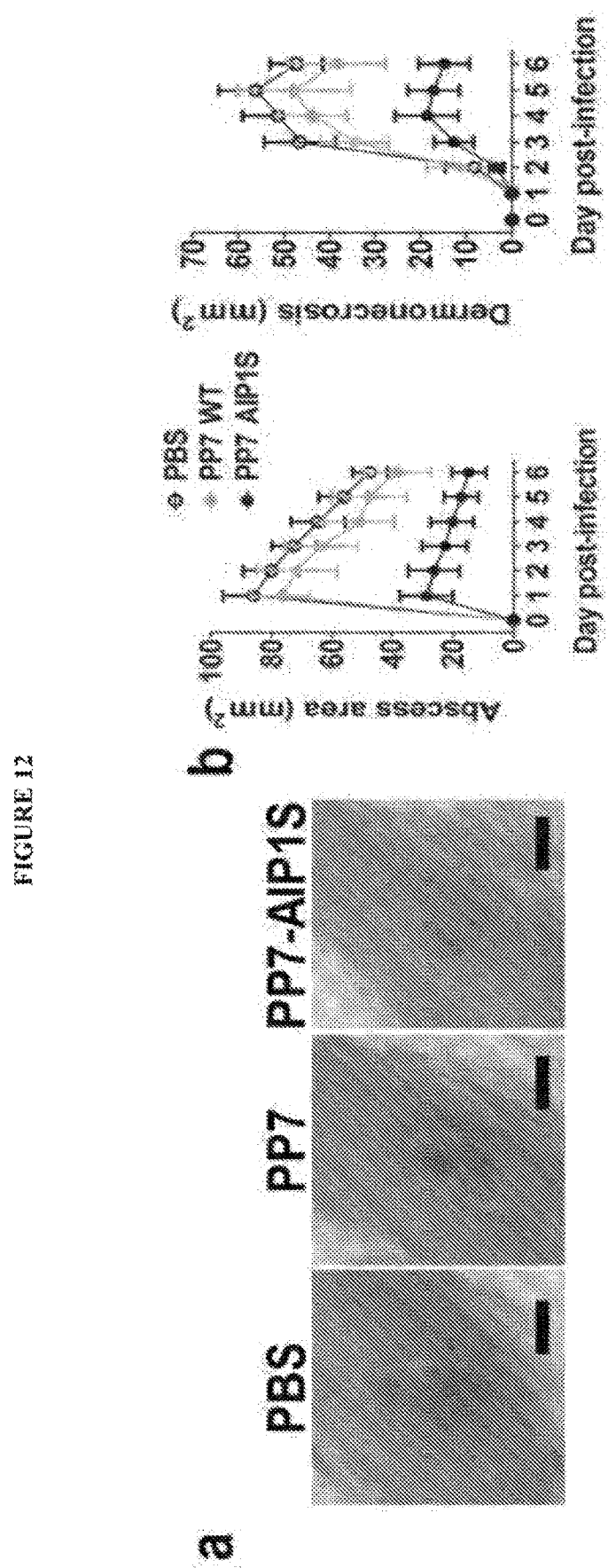
FIG. 12 shows that PP7-AIP1 S vaccination limits the severity of *S. aureus* skin infection in a mouse model of dermonecrosis. BALB/c mice were vaccinated twice (i.m.) at 4 week intervals with 10 μg of the indicated VLPs or PBS control. Eight weeks after the second vaccination, mice were challenged by subcutaneous infection with 4×10$_7$ CFU of USA300 LAC. Representative (a) day 3 images of infection site and (b) daily measures of abscess area and dermonecrosis. Calculated area under the curve (AUC) values for (c) abscess area (ANOVA $p<0.0042$), (d) dermonecrosis ($p=0.0177$) and (e) percent weight change over the six day infection, as well as (f) day 6 bacterial burden at the site of infection ($p=0.0001$) (representative of two independent experiments of n=6 mice per group). (g) Cytokine levels in clarified abscess tissue homogenate on day 6 postinfection (ANOVA IL-1β, $p=0.0587$; TNF<, $p=0.0358$) (n=6 mice per group). Data are mean±s.e.m. Newman-Keuls post-test: ns, not significant; *$p<0.05$; $p<0.01$; *$p<0.001$. Some of this data is also presented in FIGS. 6-8.
Figure 12:
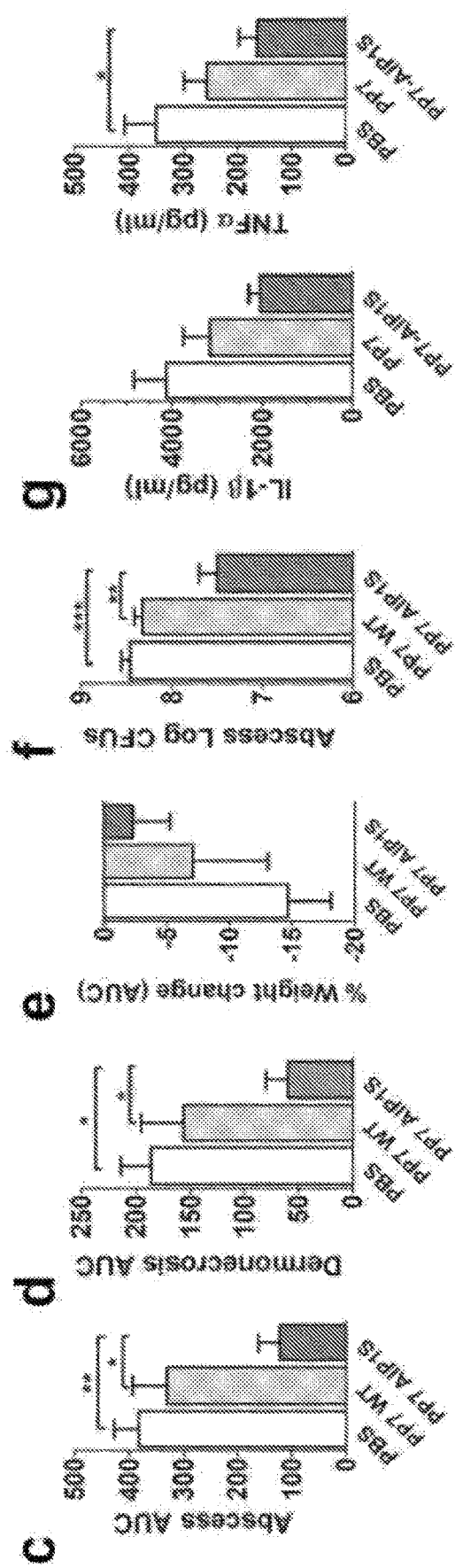
Figure 13:
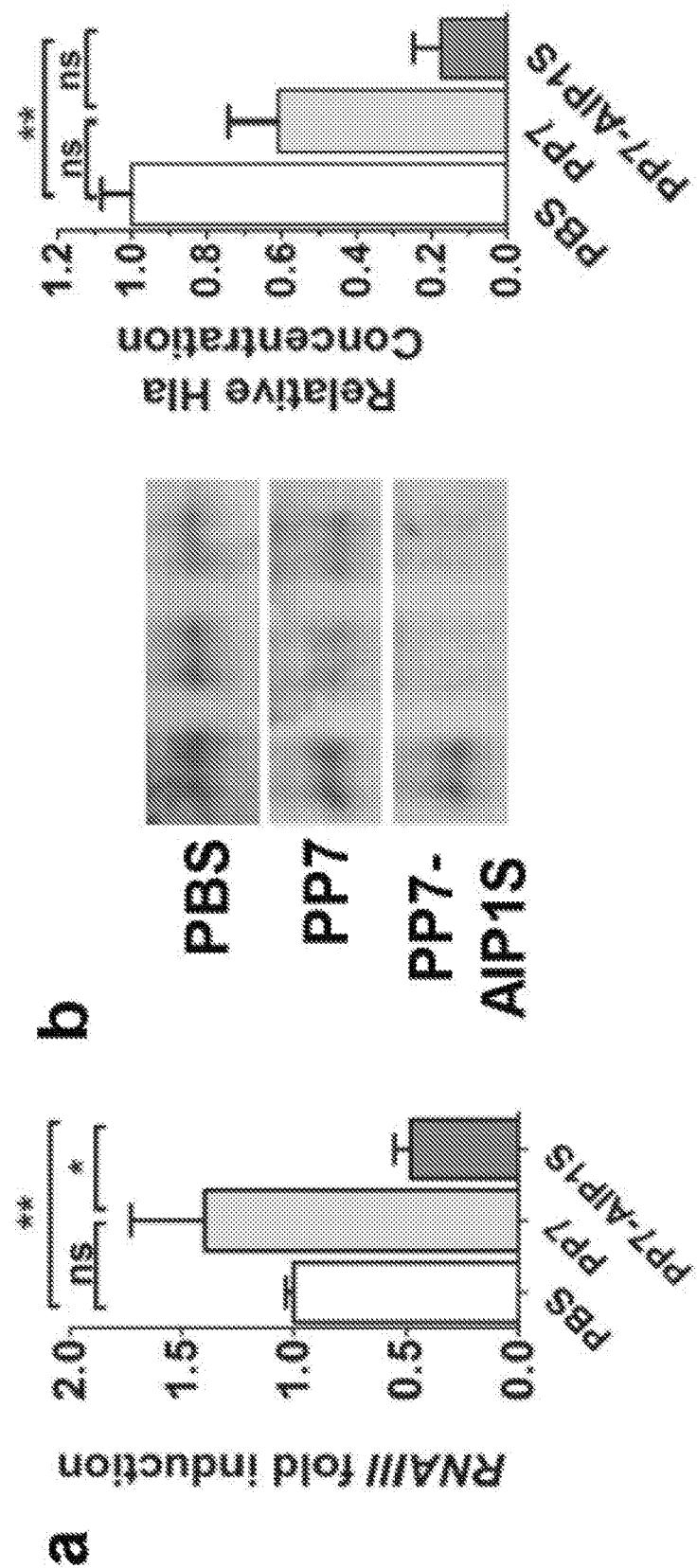
FIG. 13 shows that PP7-AIP1S vaccination limits agr function at the site of *S. aureus* infection. BALB/c mice were vaccinated twice (i.m.) at 4 week intervals with 10 μg of the indicated VLPs or PBS control. Eight weeks after the second vaccination, mice were challenged by subcutaneous infection with 4×10$_7$ CFU of USA300 LAC. (a) Local RNAIII transcription on day 1 postinfection measured by qPCR (n=4 mice per group, Kruskal-Wallis ANOVA $p=0.0029$). (b) Representative immunoblot (showing 3 replicates) and quantification of Hla levels (relative to PBS control) in clarified abscess tissue homogenate on day 6 post-infection (n=6 mice per group) (Kruskal-Wallis ANOVA $p=0.0025$) with Dunn's post-test: ns, not significant; *$p<0.05$; **$p<++0.01$.
Figure 14:
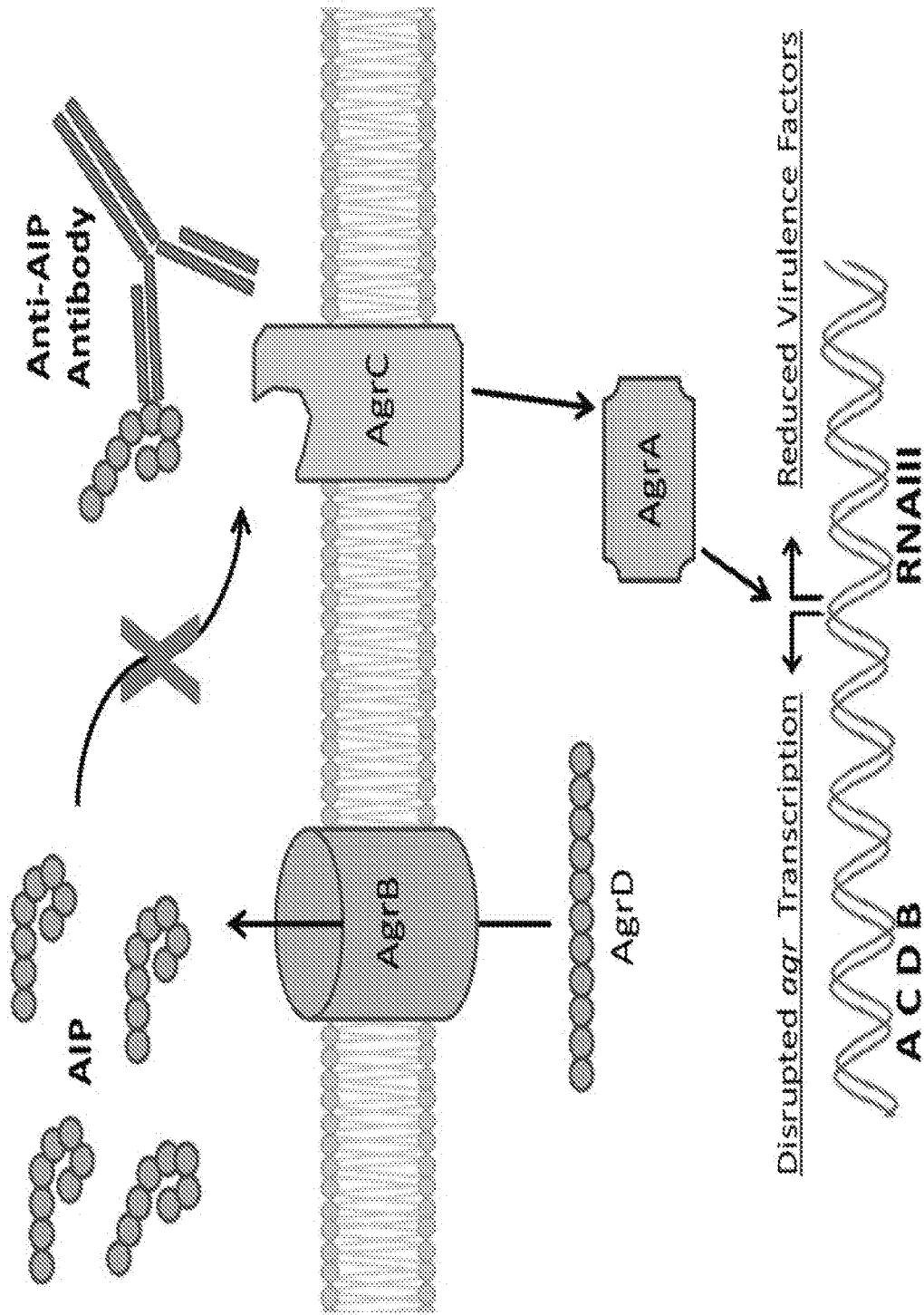
FIG. 14 shows an anti-AIP1 S antibody mechanism of action of the present invention, based upon the results of experimentation described in the Examples section hereof.

S. aureus AIP1 is an eight amino acid peptide (YSTCDFIM, SEQ ID NO: 1) cyclized by a thiolactone bond between the Cys4 side-chain and the carboxyl group of the C-terminal residue (Met8) (FIG. 10a). Given that cyclization is essential for function, immune recognition of the cyclic form of AIP1 may be necessary for antibody-mediated neutralization. However, the small size of these peptides makes them innately non-immunogenic and, together with the labile nature of the thiolactone, increases the difficulty of vaccine development[12,13,16]. The inventors sought to overcome these challenges using a bacteriophage virus-like particle (VLP) vaccine platform. These VLPs self-assemble from recombinantly expressed bacteriophage coat proteins which can be genetically altered for surface presentation of practically any epitope in a multivalent format that virtually guarantees strong immunogenicity resulting in high titer, high affinity and long-lasting antibodies[17]. Specifically, the inventors hypothesized that a vaccine produced by conformationally-restricted presentation of the AIP1 amino acid sequence on the surface of bacteriophage VLPs would elicit antibodies against native AIP1 and induce immune control of agr type I-regulated virulence, despite the absence of a thiolactone in the heterologous epitopic peptide incorporated in to the VLP.

To test this, the inventors produced a VLP-based agr type I vaccine by cloning a modified AIP1 amino acid sequence (YSTSDFIM, SEQ ID NO:2) into an immuno-prominent surface loop (the AB-loop) of the *Pseudomonas aeruginosa* RNA bacteriophage PP7 coat protein[18-21]. As expected, the resulting vaccine (PP7-AIP1 S) elicited antibodies which recognized AIP1 in vitro and was efficacious in a murine SSTI model upon challenge with a highly virulent MRSA agr type I isolate. Compared to controls, PP7-AIP1S vaccination resulted in reduced agr function and agr-regulated virulence factor production at the site of infection. Importantly, PP7-AIP1S vaccination significantly reduced *S. aureus* pathogenesis, based on dermonecrosis and weight loss, and increased bacterial clearance, findings consistent with enhanced host innate defense in the absence of agr function[8,22-26]. Together, these results demonstrate the protective benefits of vaccine-induced immune control of agr type I-regulated virulence. Given that several important pathogens utilize similar structurally constrained peptides for virulence regulation[27], the findings highlight the potential clinical utility of VLP-based vaccines targeting virulence regulators as an alternative or adjunct approach to combat infections caused by other human pathogens.

Results

Presentation of the *S. aureus* AIP1 Sequence on VLPs Induces AIP1-Recognizing Antibodies.

The icosahedral capsid of the *Pseudomonas aeruginosa* RNA bacteriophage PP7 self-assembles from coat protein monomers, with each monomer presenting a highly constrained β-turn, called the AB-loop, on the surface of the assembled capsid[21,28,29]. In an effort to promote immunogenicity and maintain the structural integrity of AIP1 presentation to the adaptive immune system, the inventors inserted a modified AIP1 sequence into the second AB-loop of the previously reported PP7 single-chain coat protein dimer which self-assembles into stable VLPs (FIG. 1a-c)[18-20,30-32]. To avoid potential intermolecular disulfide bond formation that could negatively impact VLP purification and immune presentation, the inserted AIP1 sequence included a cysteine to serine mutation in position 4 (YSTCDFIM SEQ ID NO:1 to YSTSDFIM, SEQ ID NO:2) (referred to as AIP1S). Recombinantly-expressed PP7-AIP1 S protein dimers self-assemble into soluble VLPs as indicated by a single protein band (Coomassie staining) upon agarose gel electrophoresis, and by co-migration of encapsidated RNA (ethidium bromide staining) (FIG. 1d). The resulting highly purified PP7-AIP1S VLPs consist of 90 single-chain coat protein dimers, which therefore display 90 copies of AIP1S per VLP to be presented for immune stimulation.

The inventors first sought to determine whether vaccination with PP7-AIP1S would induce production of antibodies capable of recognizing *S. aureus* AIP1. To address this, we vaccinated mice with PP7-AIP1 S (twice with a 4-week interlude) and then measured the ability of serum antibodies to specifically bind the AIP1S sequence. Serum collected at two-, four- and eight-weeks after the last vaccination with PP7-AIP1 S, but not after PP7 control vaccination, showed dose-dependent binding to the AIP1S sequence present on PP7-AIP1 S VLPs (FIG. 2a). Importantly, in competitive dose-response assays, AIP1 S binding by eight-week post-vaccination antiserum (geometric mean titer=4,550) was inhibited by synthetic cyclic AIP1, but not synthetic AIP2 (GVNACSSLF, SEQ ID NO:3) (FIG. 2b), demonstrating specificity and the ability to bind native AIP. These results, showing the production of specific antibodies which recognized soluble, native AIP1, suggested maintenance of the conformational integrity of AIP presentation within the PP7 AB-loop.

PP7-AIP1S Vaccination Provides Protection in a Murine Model of *S. aureus* Dermonecrosis.

Figure 3:
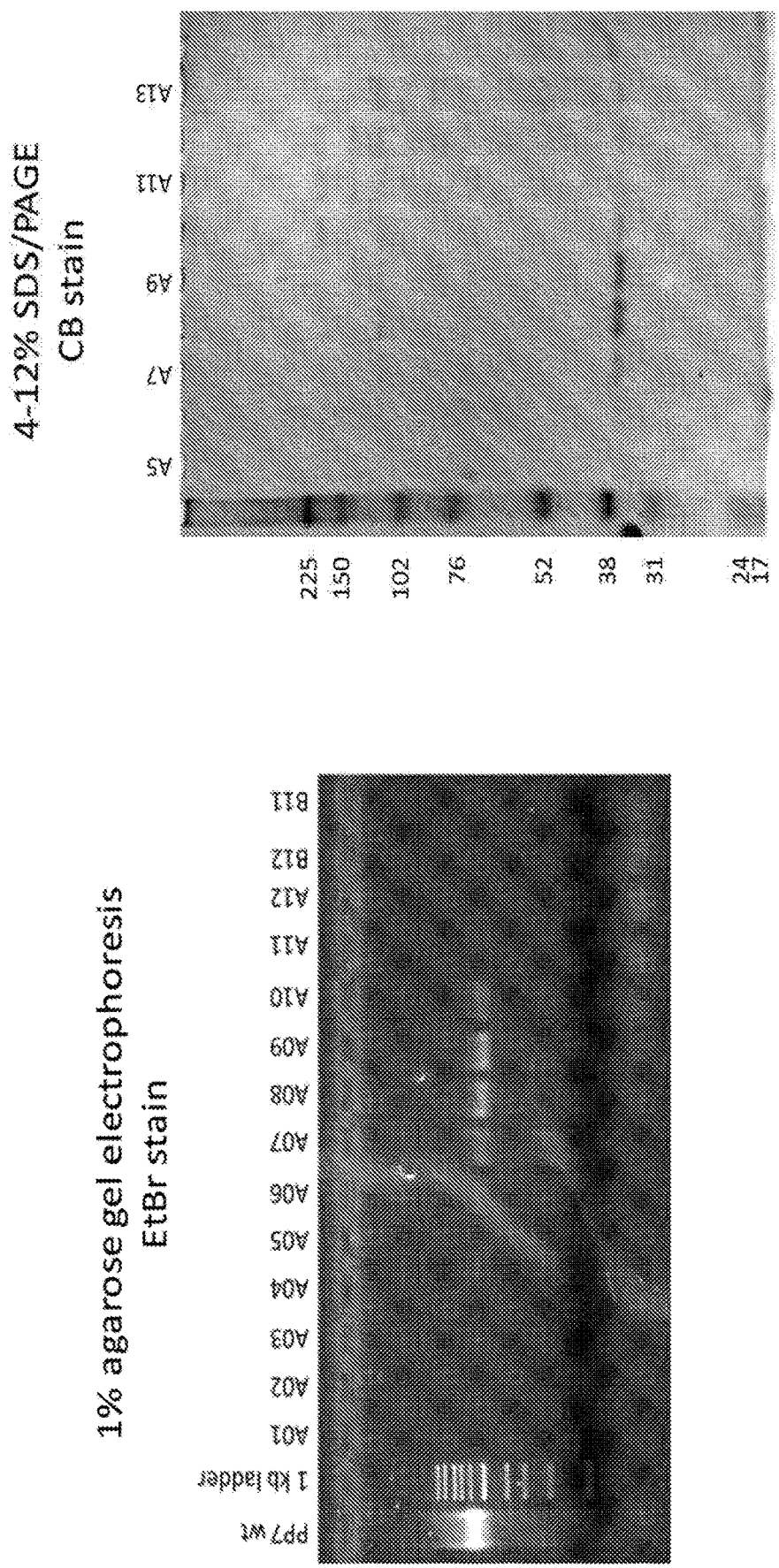
FIG. 3 shows the purity of PP7-AIP1S on 1% agarose gel electrophoresis ethidium bromide (EtBr) stain (left) and 4-12% SDS/PAGE CB Stain (right).

MRSA isolates of the pulsed-field gel electrophoresis type USA300 (agr type I) have long been the cause of most community-associated MRSA (CA-MRSA) infections, and now also cause an increasing number of health-care associated infections[33]. In mouse models of USA300 SSTI, infection with an isogenic agr-deletion mutant (Δagr) results in significantly decreased pathogenesis and increased bacterial clearance compared to infection with the wild-type agr+ strain[8,22-25]. Therefore, we postulated that vaccination with PP7-AIP1 S would induce immune suppression of agr-signaling in vivo, thus reducing pathogenesis and increasing bacterial clearance during SSTI. To evaluate the efficacy of PP7-AIP1S vaccination against agr type I-mediated virulence and to avoid potential non-specific effects of VLP administration[34], we challenged mice eight weeks after final vaccination using a well-established mouse model of *S. aureus* SSTI[35] and the highly virulent USA300 isolate LAC[36]. As expected, PP7-AIP1S vaccinated mice showed reduced abscess formation, dermonecrosis and weight loss (used as a measure of morbidity) over the course of a six-day infection compared to controls (FIG. 3a-e). Importantly, bacterial burden on day 6 post-infection was also significantly reduced in the PP7-AIP1S vaccinated group (FIG. 3f) consistent with lower local levels of the inflammatory cytokines IL-1β and TNFα (FIG. 3g). Given the contributions of agr-signaling to pathogenesis and inflammation in this infection model, these data demonstrate the efficacy of PP7-AIP1 S vaccination against *S. aureus* agr type I-regulated pathogenesis during skin infection.

PP7-AIP1S Vaccination Inhibits *S. aureus* Agr-Signaling In Vivo.

Figure 4:
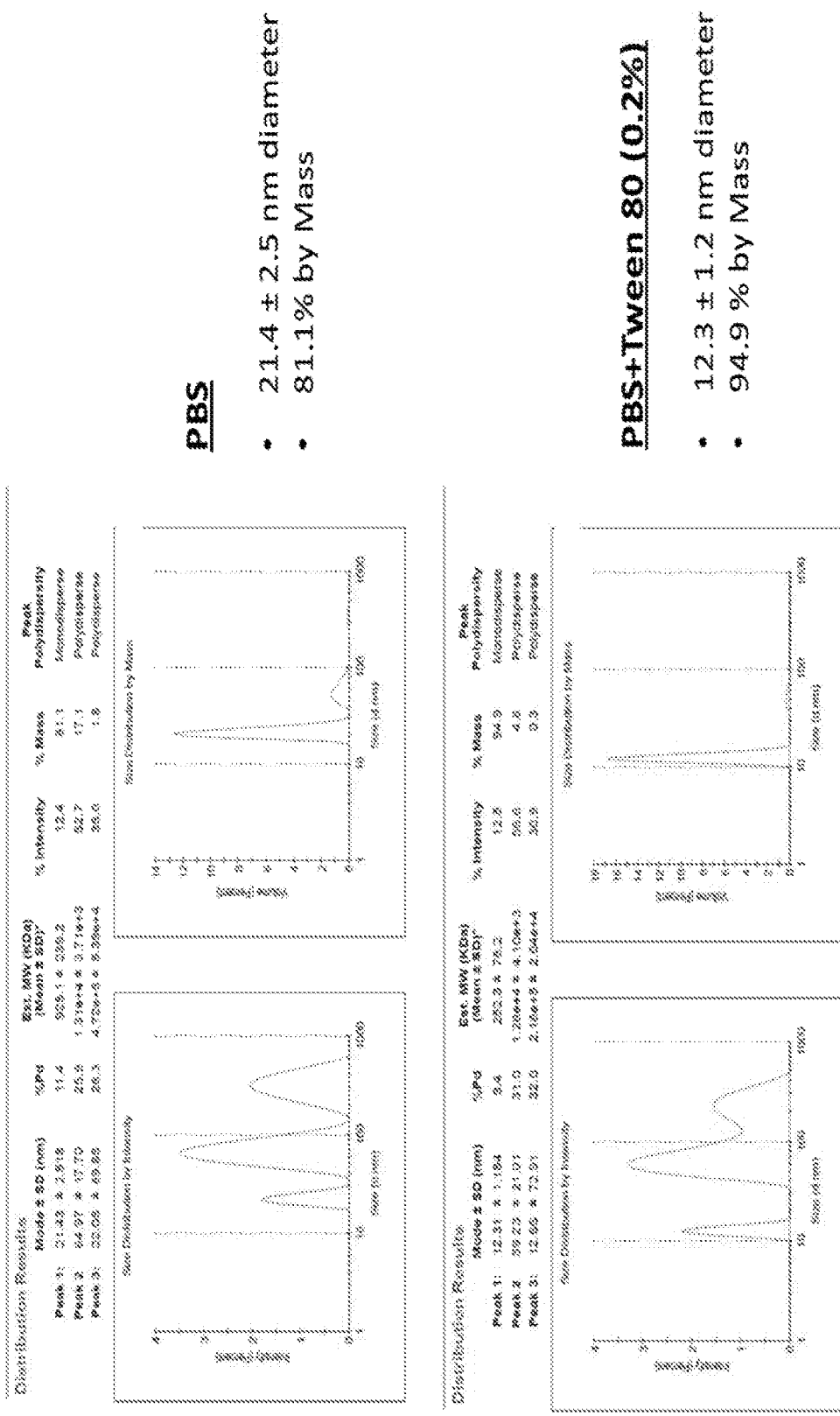
FIG. 4 shows the homogeneity of PP7-AIP1S using Malvern Zetasizer Dynamic Light Scattering in PBS (top two panels) and PBS+TWEEN 80 (0.2%).
Figure 5:
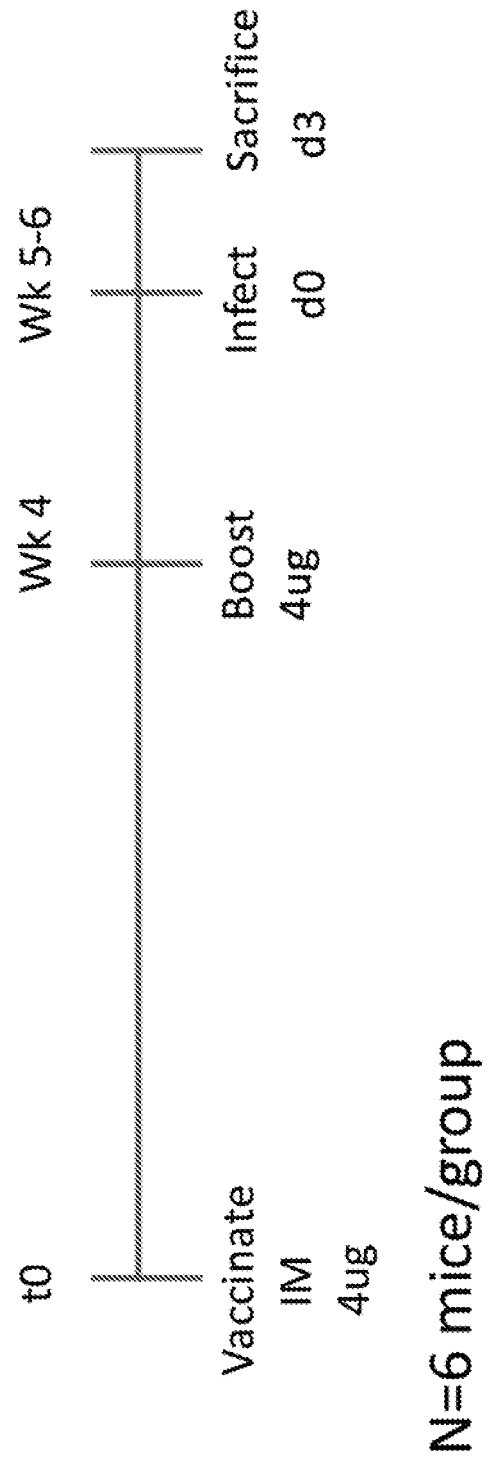
FIG. 5 shows a schematic of a vaccination schedule. Four week old female BALB/c mice were vaccinated by IM injection with PBS control, PP7 control or PP7-AIP1C4S (note that AIP1C4S and AIP1S are equivalent peptides). A boost was given 4 weeks later and mice were challenged with a SA skin infection 2 to 8 weeks after the boost.
Figure 6:
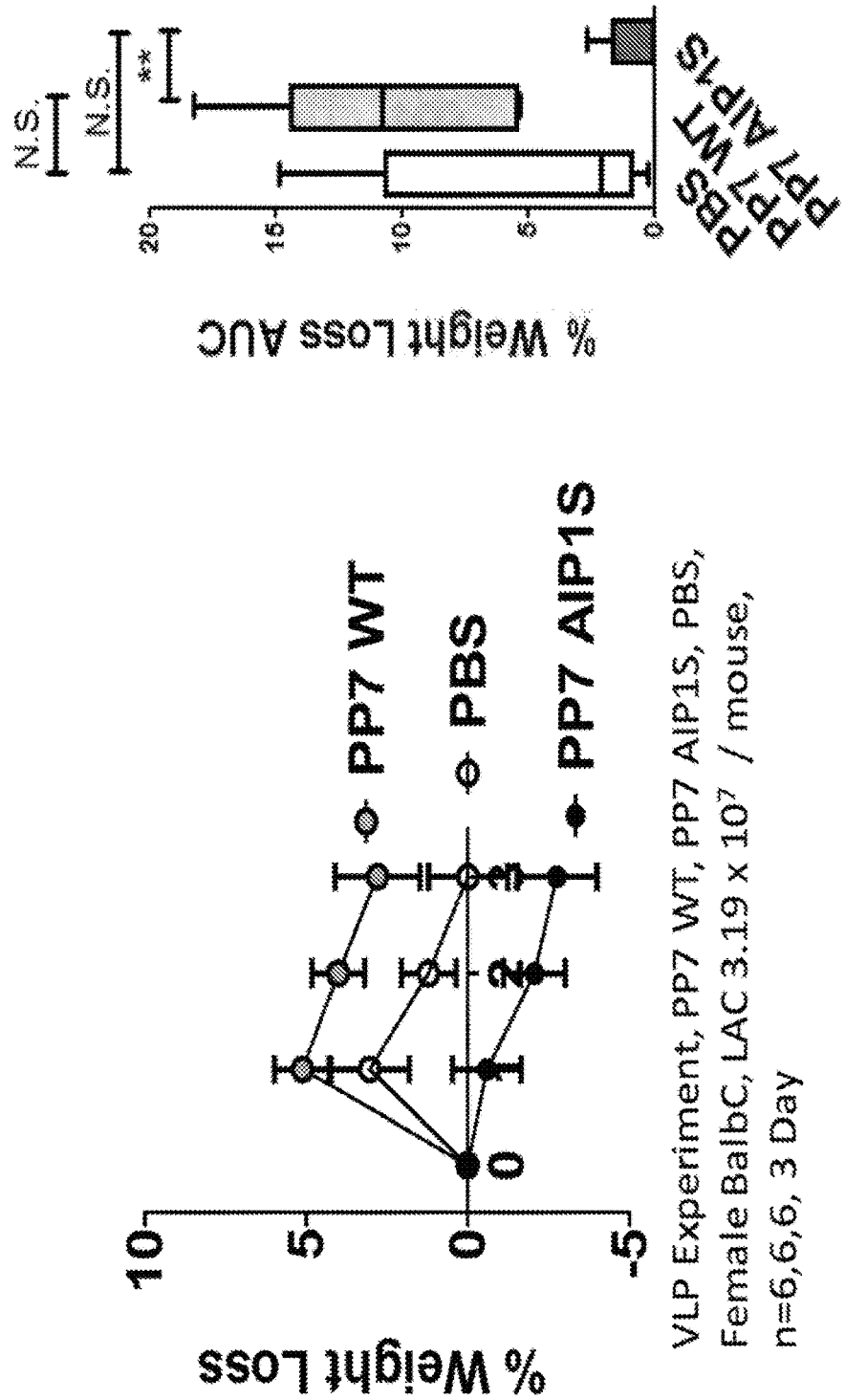
FIG. 6 shows that PP7-AIP1C4S vaccination protects mice against weight loss, used as a measure of morbidity, during skin infection challenge with agr type I MRSA.
Figure 7:
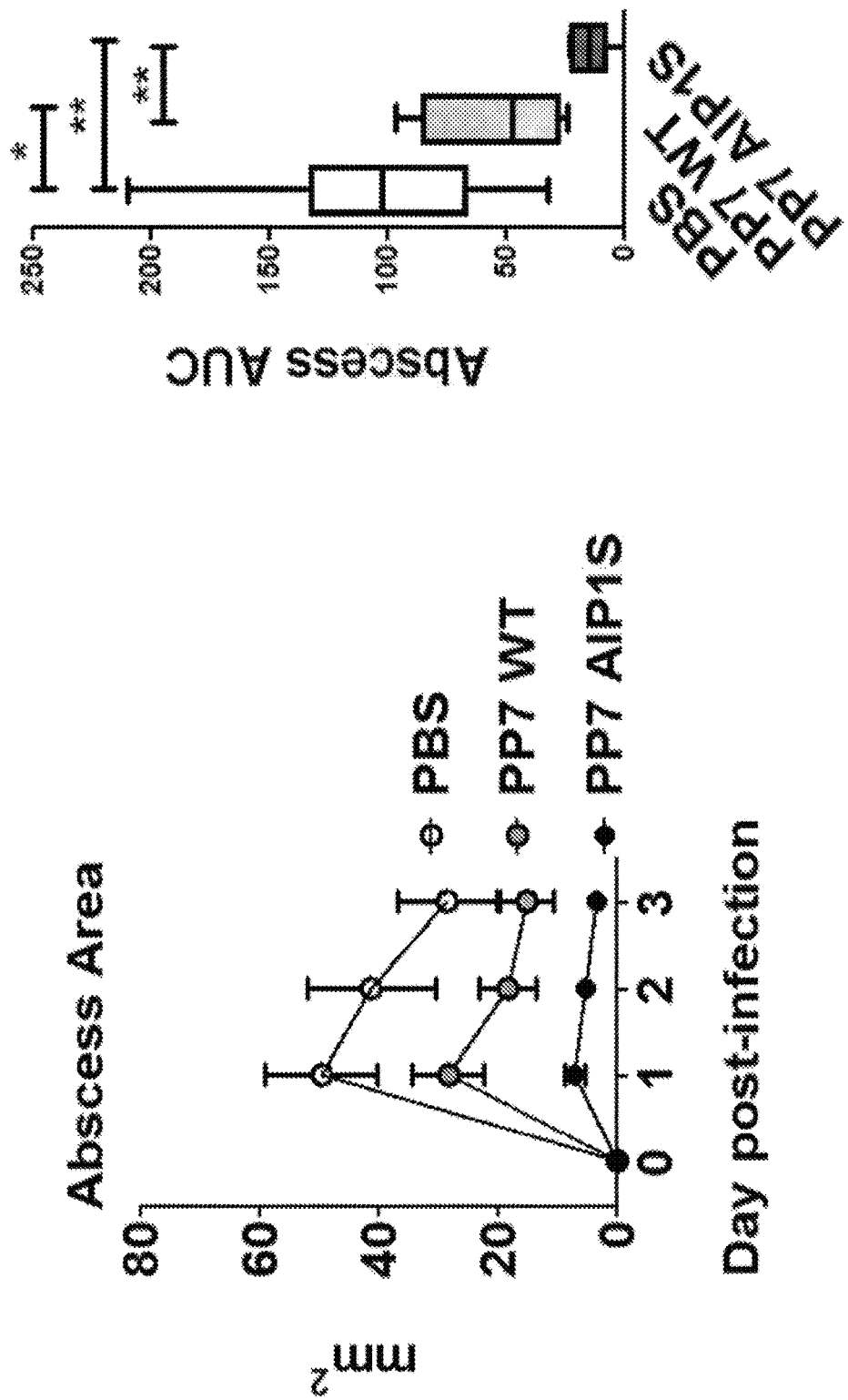
FIG. 7 shows that PP7-AIP1C4S vaccination protects mice against abscess formation, used as a measure of pathogenesis, during skin infection challenge with agr type I MRSA.
Figure 8:
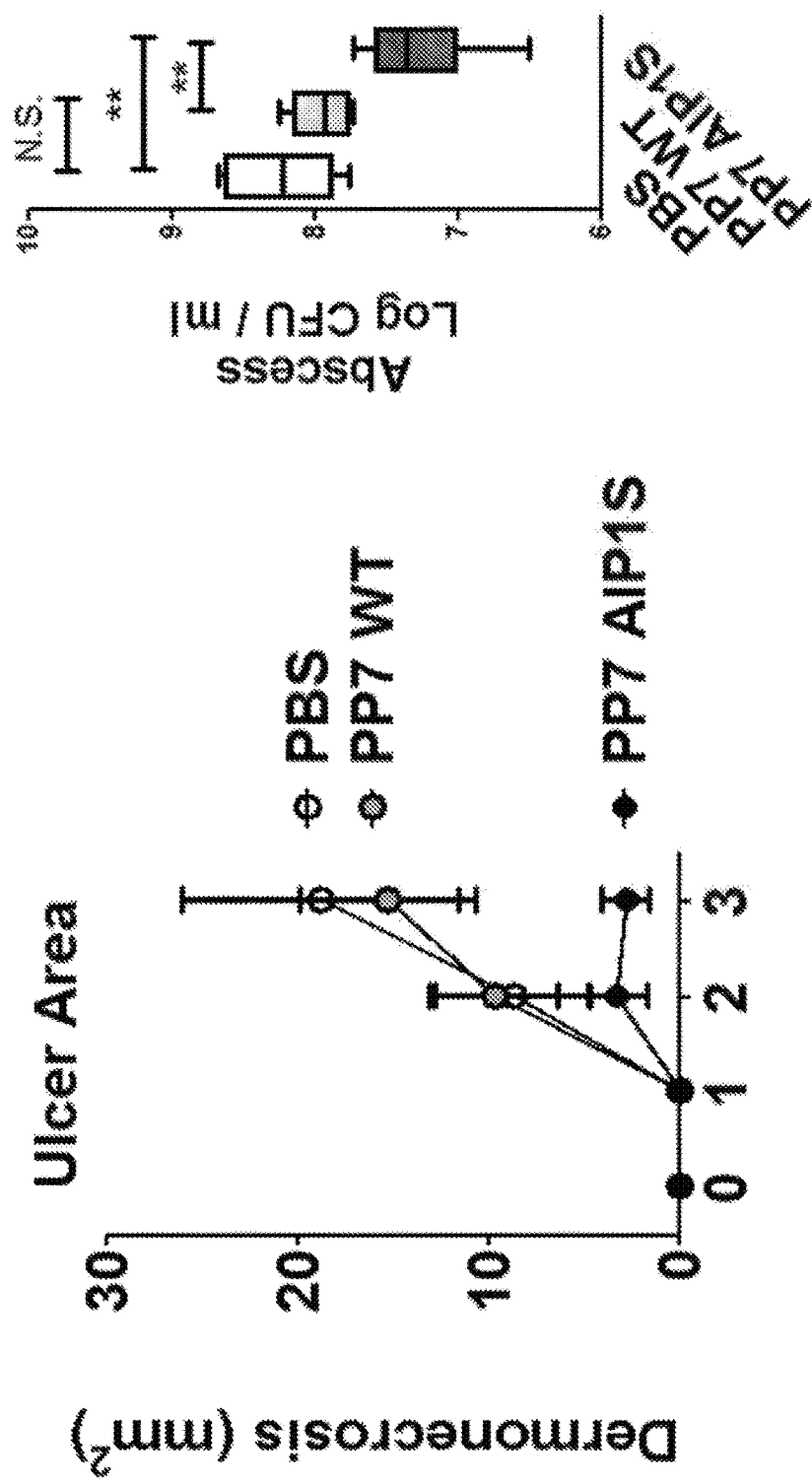
FIG. 8 shows PP7-AIP1C4S vaccination protects mice against dermonecrosis (left) during skin infection challenge with agr type I MRSA. Toxins regulated by agr are required for dermonecrosis, suggesting that vaccination with PP7-AIP1C4S induces protection against AIP signaling. PP7-AIP1C4S vaccinated mice are also better able to clear SA at the site of infection (right). This is consistent with inhibition of immune cell lytic toxins regulated by agr.

*S. aureus* agr-signaling induces expression of the effector molecule RNAIII as well as production of alpha-hemolysin (Hla), the causative agent of dermonecrosis[37-41]. The results of our challenge studies, as well as our in vitro studies showing that antibodies from PP7-AIP1S vaccinated mice bind soluble AIP1, suggested that vaccination with PP7-AIP1 S results in immune suppression of agr-signaling during *S. aureus* SSTI. If correct, we would expect reduced RNAIII transcription and Hla expression at the site of infection (local) in PP7-AIP1S vaccinated mice compared to controls. To test this, we measured local RNAIII expression and Hla protein levels on days one and six, respectively, following subcutaneous infection. As expected, RNAIII expression was reduced at the site of infection in PP7-AIP S vaccinated mice compared to controls (FIG. 4a), as were local levels of Hla (FIG. 4b). Together, these data support a mechanism of action whereby vaccination with PP7-AIP1S induces immune control of *S. aureus* agr type I signaling and virulence regulation during SSTI.

Discussion

The ongoing antibiotic resistance crisis highlights the urgent need for non-conventional approaches to combat infectious disease, including approaches to inhibit bacterial virulence[42,43]. In the case of the important human pathogen *Staphylococcus aureus*, virulence regulation is largely mediated by the agr operon via secretion of AIPs[9,10]. These small, conformationally-restrained, secreted peptides bind in an autocrine and paracrine fashion to the bacterial membrane receptor AgrC, which in turn regulate downstream virulence factor expression. Therefore, antibody-mediated sequestration of secreted AIPs could neutralize agr-signaling and virulence factor expression on a population level. Of the four S. aureus agr types, agr type I isolates are most frequently associated with invasive infection[14,15]. Here we report that multivalent, conformationally-restricted presentation of a modified AIP1 amino acid sequence on VLPs elicits immune control of S. aureus agr type I-regulated virulence. Specifically, PP7-AIP1S vaccination (1) induced the production of anti-AIP1 antibodies, (2) limited agr type I-signaling in vivo and (3) demonstrated efficacy (reduced pathogenesis and increased bacterial clearance) in a mouse model of S. aureus SSTI. Given these results and the contribution of agr type I isolates to human S. aureus infection[14,15], vaccine prevention of agr type I-mediated virulence could have a major clinical impact and make a significant contribution to the fight against antibiotic resistance.

The diversity of virulence factors produced by S. aureus[7], many of which disable innate immune cells[44-46], and the range of infection types (skin, pneumonia, bacteremia, etc.)[7,47], suggests that multiple anti-virulence approaches may be needed to limit human disease. For example, targeting specific virulence factors, in particular Hla which is a major contributor to pathogenesis[48], has shown efficacy in numerous animal models[38,39,49,52] and a monoclonal antibody targeting Hla (MEDI4893) is currently in human clinical trials[53]. Broader approaches aimed at inhibiting S. aureus virulence regulation have included peptide and small molecule targeting of the agr system[22,24,26,54-66], as well as development of a monoclonal antibody (mAb) against S. aureus AIP4[12,67]. However, agr-signaling has been shown to occur early post-infection and disruption of this early signaling correlates with reduced pathogenesis in the host[22], suggesting a possible limit to the window of opportunity for therapeutic agr-inhibition. Therefore, the development of an efficacious anti-agr vaccine could expand the impact of S. aureus virulence regulation strategies to have the broadest potential clinical benefit to patients. In this regard, we previously developed a VLP-based AIP4 mimotope vaccine by screening a VLP-peptide library against an anti-AIP4 mAb, AP4-24H11[12,13,67], shown by passive transfer to be protective in a mouse model of agr type IV SSTI. Here we advance this work by demonstrating the efficacy of PP7-AIP1S vaccination against S. aureus agr type I-regulated virulence. Our findings suggest that this VLP-based approach may be utilized to produce a combined vaccine against virulence regulation by each of the agr types, thus serving as a valuable component of an overall anti-virulence strategy.

In addition to Staphylococcal species[9,10], other human pathogens using agr-like quorum sensing systems and secreted peptides to coordinate virulence factor expression[27] could be targeted by VLP-based vaccination. For example, the food-borne pathogen Listeria monocytogenes uses a variety of communication systems to regulate virulence[68,69], including an agr locus and recently identified secreted AIP[70-74]. In L. monocytogenes, the agr system regulates over 650 genes contributing to virulence including ones involved in biofilm formation and host cell invasion[71]. Similarly, Enterococcus faecalis, an important cause of drug resistant infections[75], uses the agr-like fsr gene locus and the secreted, cyclic peptide gelatinase biosynthesis-activating pheromone (GBAP)[76,77], to regulate expression of virulence factors important for biofilm formation and pathogenesis[78-83]. Importantly, it has also recently been shown that an agr locus regulates production of toxins A and B by the multidrug resistant pathogen Clostridium difficile[84,85]. These C. difficile toxins are directly responsible for disease manifestation[86] which, in severe cases, can result in sepsis and death[87], suggesting that interference with agr-signaling by this pathogen could significantly limit disease. Therefore, a VLP-vaccine platform could provide a straight-forward approach to elicit immune inhibition of agr- and agr-like virulence signaling by these and other important human pathogens.

Virus-like particles have proven to be a flexible and highly immunogenic platform for vaccine design, and are currently used in FDA-approved vaccines[88], including Hepatitis B vaccines[89] and the current nonavalent HPV vaccine (Gardasil 9) designed to induce protection against nine HPV types[90]. Although non-replicating, the dense, repetitive array of coat proteins comprising VLPs is largely unique to microbial antigens and this multivalency triggers a robust immune response in mammals. Therefore, VLPs can dramatically increase the immunogenicity of otherwise poorly immunogenic peptides[17,91] even including self-antigens[92,93]. This property, along with the potential for presentation of conformation-dependent antigens, has resulted in investigation of VLP-based vaccines against numerous pathogenic viruses, allergies, cancer, autoimmune disease, Alzheimer's disease and chronic diseases such as hypertension[17,94-97]. However, reports of the use of VLP-based vaccines to elicit adaptive immunity against specific bacterial pathogens or proteins have come mainly from our own work and from research targeting Streptococcal species[13,98-100], suggesting that the flexibility of VLP-based vaccine approaches to address bacterial diseases remains largely untapped. Given the FDA approval and success of VLP vaccines against viral pathogens, the use of VLP-based vaccines to prevent infections by the many important human bacterial pathogens warrants further investigation.

In this era of diminishing antibiotic efficacy, a multi-pronged approach, including novel antibiotics, host-targeted therapeutics, vaccines, anti-virulence strategies and combined therapies will likely be crucial for combating disease caused by antibiotic resistant pathogens[11,42,43,101]. Here we present a novel approach to achieve vaccine induced immune control of S. aureus agr-regulated virulence. This work highlights the potential clinical utility of VLP-based vaccines as part of an overall strategy to combat infections caused by MRSA and other important antibiotic resistant human pathogens utilizing secreted peptides for virulence regulation[27].

SUMMARY

The inventors can summarize the successful results of the experimentation described herein as follows.
 VLPs can be constructed which present AIP epitopes (AIP1, AIP1S, among others) on their surface.
 Vaccination with PP7-AIP1S induces antibodies that recognize native AIP1.
 PP7-AIP1S vaccination limits pathogenesis (abscess, dermonecrosis) and promotes bacterial clearance during S. aureus SSTI.
 PP7-AIP1S vaccination limits the local pro-inflammatory cytokine response during S. aureus SSTI.
 PP7-AIP1 S vaccination disrupts agr-signaling and agr-mediated virulence.
Methods
Ethics Statement.
 Animal studies described herein were approved by the Institutional Animal Care and Use Committee (IACUC) of the University of New Mexico Health Sciences Center (Animal Welfare Assurance number D16-00228) and conducted in strict accordance to recommendations in the Guide for the Care and Use of Laboratory Animals[102], the Animal Welfare Act, and U.S. federal law.

Bacterial Strains and Growth Conditions.

The CA-MRSA USA300 isolate LAC[36] (generously provided by Dr. Frank DeLeo, Rocky Mountain National Laboratories, National Institutes of Health, Hamilton, Mont.) was used for infection studies. Early exponential-phase bacteria were prepared as previously described[103] and stored at −80° C. for no more than two weeks prior to use. For infection studies, bacteria were diluted in USP-grade saline (B. Braun Medical, Irvine, Calif.) to yield $4 \times 10^7$ CFU per 50 µL. The number of CFU was verified by plating ten-fold serial dilutions onto Trypticase soy agar containing 5% sheep blood (Becton, Dickinson and Company; Franklin Lakes, N.J.).

VLP Cloning, Expression and Purification.

The pET2P7K32 plasmid[20], encoding the PP7 single-chain dimer under the T7 promoter and transcription terminator, was used for synthesis of PP7-AIP1S VLPs in E. coli. With pET2P7K32 as a template, PCR was used to produce an insert fragment encoding a KpnI restriction site, the modified AIP1 sequence (YSTSDFIM, SEQ ID NO:2), and a downstream BamHI site (forward primer 5'-GGC GGT ACC TACAGTACCTCTGACTTCATCATG GAG GCT ACT CGC ACT CTG ACT GAG-3' (SEQ ID NO:31); reverse primer 5'-CGG GCT TTG TTA GCA GCC GG-3' (SEQ ID NO:32). The PCR fragment was cloned into the pET2P7K32 at the KpnI and BamHI restriction sites and insertion was verified by sequence analysis.

E. coli C41 cells (Lucigen, Middleton, Wis.) transformed with pET2P7K32 or the pET2P7K32-AIP1S expression plasmid were grown at 37° C. to an $OD_{600}$ of 0.8. Expression was induced with 1 mM IPTG, cells cultured for an additional 3 hours, and harvested by centrifugation. Cell pellets were lysed and VLPs purified essentially as described previously[20] but with size exclusion purification using a 16/60 Sephacryl S-400 HR column (GE Healthcare, Pittsburgh, Pa.). VLP purity was verified by agarose gel electrophoresis plus ethidium bromide and Coomassie staining. VLPs were concentrated using Amicon Ultra Centrifugal filter units (100K MWCO) (EMD Millipore, Billerica, Mass.), and concentrations determined by SDS-PAGE comparison to hen egg lysosome concentration standards (Sigma-Aldrich, St. Louis, Mo.) VLP aliquots were stored at −20° C. until use.

Mouse Immunizations.

Four week old, female BALB/cJ mice (Jackson Laboratories, Bar Harbor, Me., USA) were immunized by injection into the caudal thigh muscle with 50 µL of PBS alone or containing 10 µg of either PP7-AIP1S or PP7. Mice received an identical injection four weeks after the initial dose. Serum for ELISA analysis was collected by cardiac puncture at two, four or eight weeks after the second vaccination, with challenge experiments performed at the eight week timepoint.

ELISA.

ELISA plates to measure serum antibody binding to AIP1S were prepared by coating Ultra Cruz ELISA High Binding plates (Santa Cruz Biotechnology, Santa Cruz, Calif.) with 125 ng per well of recombinant PP7 or PP7-AIP1S in 50 µL PBS and incubating 20 hours at room temperature (RT) with shaking. After removing excess liquid, plates were blocked for 2 hours with PBS containing 0.05% Tween-20 and 1% casein. To reduce PP7- and potential E. coli-binding antibodies (depleted serum) mouse serum was treated as follows: Serum was diluted 1:50 in PBS and incubated for one hour at RT with end-over-end rotation together with recombinant PP7 (10 µg per 300 µL diluted serum) and PBS-washed C41 cells (the E. coli strain used for VLP-expression) (~$9 \times 10^6$ CFUs). The mixture was centrifuged (5 min at 11,600×g) to remove antibody bound to C41 cells, and the intermediate depleted serum processed through an Amicon Ultra Centrifugal filter unit (100K MWCO) to remove antibody bound to PP7. The final depleted serum was serially diluted onto PP7- or PP7-AIP1S-coated ELISA plates and incubated for 1 hour at RT. Murine antibodies bound to VLPs were detected using goat anti-mouse poly-HRP secondary antibody (ThermoFisher Scientific, Waltham, Mass.) and developed using 1-Step™ Ultra TMB-ELISA according to manufacturer's directions (ThermoFisher Scientific). For each serum sample and dilution, AIP1 S specific binding ($\Delta A_{450}$) was equal to the $A_{450}$ for PP7-AIP1S binding minus the $A_{450}$ for PP7 binding. For competition ELISAs, depleted serum was incubated for 1 hour at 37° C. with the indicated concentrations of AIP1 or AIP2 (BioPeptide Co., Inc., San Diego, Calif.) before addition to VLP-coated ELISA plates.

Mouse Skin Infection Model.

The mouse model of dermonecrosis was implemented essentially as previously described[35]. One to three days before infection (eight weeks after the second vaccination), Nair™ was used to depilate the right flank of the mice (site of infection). On the day of infection, mice were anesthetized by isoflurane inhalation and infected by subcutaneous injection of 50 µL of saline containing $4 \times 10^7$ CFU of LAC. Mice were weighed the day of injection and daily thereafter until sacrifice. Injection sites were photographed daily and abscess and dermonecrosis areas determined by analysis with ImageJ[104]. Six days after infection, mice were sacrificed by $CO_2$ asphyxiation and a 2.25-cm$^2$ section of skin surrounding the abscess was excised for mechanical disruption. Abscess homogenate was serially diluted and plated on sheep blood agar to determine infection site bacterial burden. The remaining homogenate was clarified by centrifugation and the clarified fraction stored at −80° C. until cytokine analysis.

Cytokine Analysis by Multiplex Assay.

Clarified abscess tissue homogenates were quick thawed at 37° C. and concentrations of the indicated cytokines determined using a BioPlex 200 system and BioPlex manager software (Bio-Rad, Hercules, Calif.) together with a custom-designed mouse multiplex assay (EMD Millipore, Billerica, Mass.) according to manufacturer's directions.

RNA Isolation from Tissue and Quantitative PCR Analysis.

For analysis of day one post-infection bacterial gene transcription, 2.25-cm$^2$ sections of skin surrounding the infection site were harvested, minced, and stored in RNAlater (Qiagen, Valencia, Calif.) at −20° C. RNA was isolated using QIAzol (Qiagen) and purified using RNeasy kits (Qiagen) according to manufacturer's directions. cDNA conversion from RNA was performed with a High Capacity cDNA Reverse Transcription Kit (Applied Biosystems, Foster City, Calif.) and specific primers for S. aureus 16S (reverse, 5'-TTC GCT CGA CTT GCA TGT A-3', SEQ ID NO:33) or RNAIII (reverse, 5'-GATGTTGTTTACGA-TAGCTTACATGC-3', SEQ ID NO:34) (Integrated DNA Technologies, Coralville, Iowa). Quantitative PCR (qPCR) was performed using a ViiA-7 RT-PCR system (Applied Biosystems), the specific primers and probes[23] for 16S (forward primer, 5'-TGA TCC TGG CTC AGG ATG A-3', SEQ ID NO:35; reverse primer above and probe 5'-CGC TGG CGG CGT GCC TA-3', SEQ ID NO:36) and RNAIII (forward primer, 5'-AAT TAG CAA GTG AGT AAC ATT TGC TAG T-3',SEQ ID NO:37; reverse primer above and probe 5'-AGT TAG TT CCT TGG ACT CAG TGC TAT GTA TTT TTC TT-3', SEQ ID NO:38) (Integrated DNA Technologies) and TaqMan Gene Expression Master Mix according to the manufacturer's protocol (Applied Biosystems). Data are shown as the fold expression of RNAIII versus 16S and relative to the PBS control.

Tissue Hla Quantification by Western Blot.

For Western blot analysis of Hla levels in clarified abscess homogenate, frozen samples were quick thawed and equal amounts of total protein (based on $A_{280}$) were electrophoresed on 16% Tris-glycine SDS-PAGE gels (Life Technologies, Grand Island, N.Y.). Following transfer to polyvinylidene fluoride membrane, membranes were blocked overnight at 4° C. with TBST (20 mM Tris, pH 7.5, 150 mM NaCl, 0.1% Tween 20) with 5% nonfat dry milk. Hla was detected using sheep anti-Hla primary antibody (ab15948, Abcam, Cambridge, Mass.) and alkaline phosphatase-conjugated rabbit polyclonal anti-sheep secondary. Membranes were developed with nitroblue tetrazolium (NBT)/5-bromo-4-chloro-3-indolyl-phosphate (BCIP) (Thermo Scientific). Band intensity relative to recombinant Hla control was measured on a FluorChem R system using AlphaView software (ProteinSimple, San Jose, Calif.).

Statistical Analysis.

GraphPad Prism version 5.04 (GraphPad Software, San Diego Calif.) was used for all statistical evaluations. One-way ANOVA parameters followed Bartlett's test for equal variances and were used with Bonferroni's (ANOVA) or Dunn's (Kruskal-Wallis test, non-parametrics) post-hoc multiple comparison analyses. Results were considered statistically significant at $p<0.05$.

REFERENCES

1 Lee, G. C. et al. Incidence and Cost of Skin and soft Tissue Infections In the united States. *Value Health* 18, doi: 10.1016/j.jval.2015.03.1424 (2015).
2 Moran, G. J. et al. Methicillin-resistant *S. aureus* infections among patients in the emergency department. *N. Engl. J. Med.* 355, 666-674, doi:10.1056/NEJMoa055356 (2006).
3 Talan, D. A. et al. Comparison of *Staphylococcus aureus* from skin and soft-tissue infections in US emergency department patients, 2004 and 2008. *Clin. Infect. Dis.* 53, 144-149, doi:10.1093/cid/cir308 (2011).
4 Labreche, M. J. et al. Treatment failure and costs in patients with methicillin-resistant *Staphylococcus aureus* (MRSA) skin and soft tissue infections: a South Texas Ambulatory Research Network (STARNet) study. *J. Am. Board Fam. Med.* 26, 508-517, doi: 10.3122/jabfm.2013.05.120247 (2013).
5 Montgomery, C. P., David, M. Z. & Daum, R. S. Host factors that contribute to recurrent staphylococcal skin infection. *Curr. Opin. Infect. Dis.* 28, 253-258, doi: 10.1097/QCO.0000000000000156 (2015).
6 Fowler, V. G., Jr. & Proctor, R. A. Where does a *Staphylococcus aureus* vaccine stand? *Clin. Microbiol. Infect.* 20 Suppl 5, 66-75, doi:10.1111/1469-0691.12570 (2014).
7 Cheung, G. Y., Wang, R., Khan, B. A., Sturdevant, D. E. & Otto, M. Role of the accessory gene regulator agr in community-associated methicillin-resistant *Staphylococcus aureus* pathogenesis. *Infect. Immun.* 79, 1927-1935, doi:10.1128/IAI.00046-11 (2011).
8 Montgomery, C. P., Boyle-Vavra, S. & Daum, R. S. Importance of the global regulators Agr and SaeRS in the pathogenesis of CA-MRSA USA300 infection. *PLoS One* 5, e15177, doi:10.1371/journal.pone.0015177 (2010).
9 Novick, R. P. & Geisinger, E. Quorum sensing in staphylococci. *Annu. Rev. Genet.* 42, 541-564, doi:10.1146/annurev.genet.42.110807.091640 (2008).
10 Thoendel, M., Kavanaugh, J. S., Flack, C. E. & Horswill, A. R. Peptide signaling in the staphylococci. *Chem. Rev.* 111, 117-151, doi:10.1021/cr100370n (2011).
11 Kaufmann, G. F., Park, J. & Janda, K. D. Bacterial quorum sensing: a new target for anti-infective immunotherapy. *Expert Opin. Biol. Ther.* 8, 719-724, doi: 10.1517/14712598.8.6.719 (2008).
12 Park, J. et al. Infection control by antibody disruption of bacterial quorum sensing signaling. *Chem. Biol.* 14, 1119-1127, doi:10.1016/j.chembiol.2007.08.013 (2007).
13 O'Rourke, J. P. et al. Development of a mimotope vaccine targeting the *Staphylococcus aureus* quorum sensing pathway. *PLoS One* 9, e111198, doi:10.1371/journal.pone.0111198 (2014).
14 Jarraud, S. et al. Relationships between *Staphylococcus aureus* genetic background, virulence factors, agr groups (Alleles), and human disease. *Infect. Immun.* 70, 631-641, doi:Doi 10.1128/Iai.70.2.631-641.2002 (2002).
15 Traber, K. E. et al. agr function in clinical *Staphylococcus aureus* isolates. *Microbiology* 154, 2265-2274, doi: 10.1099/mic.0.2007/011874-0 (2008).
16 Kaufmann, G. F., Park, J., Mayorov, A. V., Kubitz, D. M. & Janda, K. D. Generation of quorum quenching antibodies. *Methods Mol. Biol.* 692, 299-311, doi: 10.1007/978-1-60761-971-0_22 (2011).
17 Chackerian, B. Virus-like particles: flexible platforms for vaccine development. *Expert review of vaccines* 6, 381-390 (2007).
18 Caldeira, J. C. & Peabody, D. S. Thermal stability of RNA phage virus-like particles displaying foreign peptides. *Journal of nanobiotechnology* 9, 22-3155-3159-3122 (2011).
19 Caldeira, J. C. & Peabody, D. S. Stability and assembly in vitro of bacteriophage PP7 virus-like particles. *J Nanobiotechnology* 5, 10, doi: 10.1186/1477-3155-5-10 (2007).
20 Caldeira Jdo, C., et al. Immunogenic display of diverse peptides, including a broadly cross-type neutralizing human papillomavirus L2 epitope, on virus-like particles of the RNA bacteriophage PP7. *Vaccine* 28, 4384-4393, doi: 10.1016/j.vaccine.2010.04.049 (2010).
21 Chao, J. A., Patskovsky, Y., Almo, S. C. & Singer, R. H. Structural basis for the coevolution of a viral RNA-protein complex. *Nat. Struct. Mol. Biol.* 15, 103-105, doi: 10.1038/nsmb1327 (2008).
22 Wright, J. S., 3rd, Jin, R. & Novick, R. P. Transient interference with staphylococcal quorum sensing blocks abscess formation. *Proc. Natl. Acad. Sci. U.S.A.* 102, 1691-1696, doi: 10.1073/pnas.0407661102 (2005).
23 Peterson, M. M. et al. Apolipoprotein B Is an innate barrier against invasive *Staphylococcus aureus* infection. *Cell Host Microbe* 4, 555-566, doi: 10.1016/j.chom.2008.10.001 (2008).
24 Sully, E. K. et al. Selective chemical inhibition of agr quorum sensing in *Staphylococcus aureus* promotes host defense with minimal impact on resistance. *PLoS Pathog.* 10, e1004174, doi:10.1371/journal.ppat. 1004174 (2014).
25 Hall, P. R. et al. Nox2 modification of LDL is essential for optimal apolipoprotein B-mediated control of agr type III *Staphylococcus aureus* quorum-sensing. *PLoS Pathog.* 9, e1003166, doi: 10.1371/journal.ppat.1003166 (2013).
26 Daly, S. M. et al. omega-Hydroxyemodin limits *Staphylococcus aureus* quorum sensing-mediated pathogenesis 27. and inflammation. *Antimicrob. Agents Chemother.* 59, 2223-2235, doi: 10.1128/AAC.04564-14 (2015).
27. Gray, B., Hall, P. & Gresham, H. Targeting agr- and agr-Like quorum sensing systems for development of common therapeutics to treat multiple gram-positive bacterial infections. *Sensors* 13, 5130-5166, doi:10.3390/s130405130 (2013).
28. Tars, K., Fridborg, K., Bundule, M. & Liljas, L. The three-dimensional structure of bacteriophage PP7 from *Pseudomonas aeruginosa* at 3.7-A resolution. *Virology* 272, 331-337, doi:10.1006/viro.2000.0373 (2000).
29. Tars, K., Fridborg, K., Bundule, M. & Liljas, L. Structure determination of bacteriophage PP7 from *Pseudomonas aeruginosa*: from poor data to a good map. *Acta Crystallogr. D Biol. Crystallogr.* 56, 398-405 (2000).
30. Tumban, E., Peabody, J., Peabody, D. S. & Chackerian, B. A pan-HPV vaccine based on bacteriophage PP7 VLPs displaying broadly cross-neutralizing epitopes from the HPV minor capsid protein, L2. *PLoS One* 6 (2011).
31. Ko, J., Park, H., Heo, L. & Seok, C. GalaxyWEB server for protein structure prediction and refinement. *Nucleic Acids Res.* 40, W294-297, doi:10.1093/nar/gks493 (2012).
32. Park, H., Lee, G. R., Heo, L. & Seok, C. Protein loop modeling using a new hybrid energy function and its application to modeling in inaccurate structural environments. *PLoS One* 9, e113811, doi:10.1371/journal.pone.0113811 (2014).
33. Carrel, M., Perencevich, E. N. & David, M. Z. USA300 Methicillin-Resistant *Staphylococcus aureus*, United States, 2000-2013. *Emerg. Infect. Dis.* 21, 1973-1980, doi:10.3201/eid2111.150452 (2015).
34. Rynda-Apple, A. et al. Virus-like particle-induced protection against MRSA pneumonia is dependent on IL-13 and enhancement of phagocyte function. *The American journal of pathology* 181, 196-210 (2012).
35. Malachowa, N., Kobayashi, S. D., Braughton, K. R. & DeLeo, F. R. Mouse model of *Staphylococcus aureus* skin infection. *Methods Mol. Biol.* 1031, 109-116, doi: 10.1007/978-1-62703-481-4_14 (2013).
36. Public health dispatch: outbreaks of community-associated methicillin-resistant *Staphylococcus aureus* skin infections—Los Angeles County, Calif., 2002-2003. *Can. Commun. Dis. Rep.* 29, 110-112 (2003).
37. Inoshima, N., Wang, Y. & Bubeck Wardenburg, J. Genetic requirement for ADAM10 in severe *Staphylococcus aureus* skin infection. *J. Invest. Dermatol.* 132, 1513-1516, doi:10.1038/jid.2011.462 (2012).
38. Kennedy, A. D. et al. Targeting of alpha-hemolysin by active or passive immunization decreases severity of USA300 skin infection in a mouse model. *J Infect Dis* 202, 1050-1058, doi:10.1086/656043 (2010).
39. Sampedro, G. R. et al. Targeting *Staphylococcus aureus* alpha-toxin as a novel approach to reduce severity of recurrent skin and soft-tissue infections. *J Infect Div* 210, 1012-1018, doi:10.1093/infdis/jiu223 (2014).
40. Kobayashi, S. D. et al. Comparative analysis of USA300 virulence determinants in a rabbit model of skin and soft tissue infection. *J Infect Dis* 204, 937-941, doi:10.1093/infdis/jir441 (2011).
41. Berube, B. J. & Bubeck Wardenburg, J. *Staphylococcus aureus* alpha-toxin: nearly a century of intrigue. *Toxins (Basel)* 5, 1140-1166 (2013).
42. *NIAID Antimicrobial Resistance Program: Current Status and Future Directions* 2014— ARstrategicplan2014.pdf, <http://www.ncbi.nlm.nih.gov/pubmed/> (2015).
43. Spellberg, B., Bartlett, J. G. & Gilbert, D. N. The future of antibiotics and resistance. *N. Engl. J. Med.* 368, 299-302, doi:10.1056/NEJMp1215093 (2013).
44. DeLeo, F. R., Diep, B. A. & Otto, M. Host defense and pathogenesis in *Staphylococcus aureus* infections. *Infect. Dis. Clin. North Am.* 23, 17-34 (2009).
45. Cheung, G. Y. & Otto, M. The potential use of toxin antibodies as a strategy for controlling acute *Staphylococcus aureus* infections. *Expert Opin. Ther. Targets* 16, 601-612 (2012).
46. Tkaczyk, C. et al. *Staphylococcus aureus* alpha toxin suppresses effective innate and adaptive immune responses in a murine dermonecrosis model. *PLoS One* 8, e75103, doi:10.1371/journal.pone.0075103 (2013).
47. Proctor, R. A. Recent developments for *Staphylococcus aureus* vaccines: clinical and basic science challenges. *European cells & materials* 30, 315-326 (2015).
48. Berube, B. J. & Wardenburg, J. B. *Staphylococcus aureus* alpha-Toxin: Nearly a Century of Intrigue. *Toxins (Basel)* 5, 1140-1166, doi:DOI 10.3390/toxins5061140 (2013).
49. Bubeck Wardenburg, J. & Schneewind, O. Vaccine protection against *Staphylococcus aureus* pneumonia. *J. Exp. Med.* 205, 287-294, doi: 10.1084/jem.20072208 (2008).
50. Adhikari, R. P. et al. Novel structurally designed vaccine for *S. aureus* alpha-hemolysin: protection against bacteremia and pneumonia. *PLoS One* 7, e38567, doi:10.1371/journal.pone.0038567 (2012).
51. Oscherwitz, J., Munoz-Planillo, R., Yu, F., Nunez, G. & Cease, K. B. In vivo mapping of a protective linear neutralizing epitope at the N-terminus of alpha hemolysin from *Staphylococcus aureus*. *Mol. Immunol.* 60, 62-71 (2014).
52. Oscherwitz, J. & Cease, K. B. Identification and validation of a linear protective neutralizing epitope in the beta-pore domain of alpha toxin. *PLoS One* 10, e0116882, doi: 10.1371/journal.pone.0116882 (2015).
53. Yu, X. Q. et al. Safety, Tolerability, and Pharmacokinetics of MEDI4893, an Investigational, ExtendedHalf-Life, Anti-*Staphylococcus aureus* Alpha-Toxin Human Monoclonal Antibody, in Healthy Adults. *Antimicrob. Agents Chemother.*, doi: 10.1128/aac.01020-16 (2016).
54. Figueroa, M. et al. Polyhydroxyanthraquinones as Quorum Sensing Inhibitors from the Guttates of *Penicillium restrictum* and Their Analysis by Desorption Electrospray Ionization Mass Spectrometry. *J. Nat. Prod.* 77, 1351-1358, doi:Doi 10.1021/Np5000704 (2014).
55. Khodaverdian, V. et al. Discovery of Antivirulence Agents against Methicillin-Resistant *Staphylococcus aureus*. *Antimicrob. Agents Chemother.* 57, 3645-3652 (2013).
56. Kuo, D. et al. Novel quorum-quenching agents promote methicillin-resistant *Staphylococcus aureus* (MRSA) wound healing and sensitize MRSA to beta-lactam antibiotics. *Antimicrob. Agents Chemother.* 59, 1512-1518, doi: 10.1128/AAC.04767-14 (2015).
57. Yu, G., Kuo, D., Shoham, M. & Viswanathan, R. Combinatorial synthesis and in vitro evaluation of a biaryl hydroxyketone library as antivirulence agents against MRSA. *ACS combinatorial science* 16, 85-91, doi: 10.1021/co400142t (2014).
58. Cech, N. B., Junio, H. A., Ackermann, L. W., Kavanaugh, J. S. & Horswill, A. R. Quorum quenching and antimicrobial activity of goldenseal (*Hydrastis canadensis*) against methicillin-resistant *Staphylococcus aureus* (MRSA). *Planta Med.* 78, 1556-1561, doi: 0.1055/s-0032-1315042 (2012).

59 Quave, C. L. et al. *Castanea sativa* (European Chestnut) Leaf Extracts Rich in Ursene and Oleanene Derivatives Block *Staphylococcus aureus* Virulence and Pathogenesis without Detectable Resistance. *PLoS One* 10, e0136486, doi: 10.1371/journal.pone.0136486 (2015).

60 Vermote, A. et al. Hamamelitannin Analogues that Modulate Quorum Sensing as Potentiators of Antibiotics against *Staphylococcus aureus*. *Angew. Chem. Int. Ed. Engl.* 55, 6551-6555, doi:10.1002/anie.201601973 (2016).

61 Nakayama, J. et al. Ambuic acid inhibits the biosynthesis of cyclic peptide quormones in gram-positive bacteria. *Antimicrob. Agents Chemother.* 53, 580-586, doi: 10.1128/AAC.00995-08 (2009).

62 Tal-Gan, Y., Stacy, D. M., Foegen, M. K., Koenig, D. W. & Blackwell, H. E. Highly potent inhibitors of quorum sensing in *Staphylococcus aureus* revealed through a systematic synthetic study of the group-III autoinducing peptide. *J. Am. Chem. Soc.* 135, 7869-7882, doi:10.1021/ja3112115 (2013).

63 Tal-Gan, Y., Ivancic, M., Cornilescu, G., Yang, T. & Blackwell, H. E. Highly Stable, Amide-Bridged Autoinducing Peptide Analogues that Strongly Inhibit the AgrC Quorum Sensing Receptor in *Staphylococcus aureus*. *Angew. Chem. Int. Ed. Engl.* 55, 8913-8917, doi: 10.1002/anie.201602974 (2016).

64 Gordon, C. P., Williams, P. & Chan, W. C. Attenuating *Staphylococcus aureus* virulence gene regulation: a medicinal chemistry perspective. *J. Med. Chem.* 56, 1389-1404 (2013).

65 Murray, E. J. et al. Targeting *Staphylococcus aureus* quorum sensing with nonpeptidic small molecule inhibitors. *J. Med. Chem.* 57, 2813-2819, doi:10.1021/jm500215s (2014).

66 Chan, W. C., Coyle, B. J. & Williams, P. Virulence regulation and quorum sensing in staphylococcal infections: competitive AgrC antagonists as quorum sensing inhibitors. *J. Med. Chem.* 47, 4633-4641, doi:10.1021/jm0400754 (2004).

67 Kirchdoerfer, R. N. et al. Structural basis for ligand recognition and discrimination of a quorum-quenching antibody. *J Biol Chem* 286, 17351-17358, doi:10.1074/jbc.M111.231258 (2011).

68 Freitag, N. E., Port, G. C. & Miner, M. D. *Listeria monocytogenes*—from saprophyte to intracellular pathogen. *Nat. Rev. Microbiol.* 7, 623-628, doi:10.1038/nrmicro2171 (2009).

69 Garmyn, D., Gal, L., Lemaitre, J. P., Hartmann, A. & Piveteau, P. Communication and autoinduction in the species *Listeria monocytogenes*: A central role for the agr system. *Commun. Integr. Biol.* 2, 371-374 (2009).

70 Autret, N., Raynaud, C., Dubail, I., Berche, P. & Charbit, A. Identification of the agr locus of *Listeria monocytogenes*: role in bacterial virulence. *Infect. Immun.* 71, 4463-4471 (2003).

71 Riedel, C. U. et al. AgrD-dependent quorum sensing affects biofilm formation, invasion, virulence and global gene expression profiles in *Listeria monocytogenes*. *Mol. Microbiol.* 71, 1177-1189, doi:10.1111/j.1365-2958.2008.06589.x (2009).

72 Rieu, A., Weidmann, S., Garmyn, D., Piveteau, P. & Guzzo, J. Agr system of *Listeria monocytogenes* EGD-e: role in adherence and differential expression pattern. *Appl. Environ. Microbiol.* 73, 6125-6133, doi:10.1128/aem.00608-07 (2007).

73 Rieu, A. et al. *Listeria monocytogenes* EGD-e biofilms: no mushrooms but a network of knitted chains. *Appl. Environ. Microbiol.* 74, 4491-4497, doi:10.1128/aem.00255-08 (2008).

74 Zetzmann, M., Sanchez-Kopper, A., Waidmann, M. S., Blombach, B. & Riedel, C. U. Identification of the agr Peptide of *Listeria monocytogenes*. *Front. Microbiol.* 7, 989, doi: 10.3389/fmicb.2016.00989 (2016).

75 Gilmore, M. S., Clewell, D. B., Ike, Y. & Shankar, N. *Enterococci*. (Massachusetts Eye and Ear Infirmary, 2014).

76 Nakayama, J. et al. Gelatinase biosynthesis-activating pheromone: a peptide lactone that mediates a quorum sensing in *Enterococcus faecalis*. *Mol. Microbiol.* 41, 145-154 (2001).

77 Nakayama, J. et al. Revised model for *Enterococcus faecalis* fsr quorum-sensing system: the small open reading frame fsrD encodes the gelatinase biosynthesis-activating pheromone propeptide corresponding to staphylococcal agrd. *J. Bacteriol.* 188, 8321-8326, doi:10.1128/jb.00865-06 (2006).

78 Cook, L. C. & Federle, M. J. Peptide pheromone signaling in *Streptococcus* and *Enterococcus*. *FEMS Microbiol. Rev.* 38, 473-492, doi:10.1111/1574-6976.12046 (2014).

79 Hancock, L. E. & Perego, M. The *Enterococcus faecalis* fsr two-component system controls biofilm development through production of gelatinase. *J. Bacteriol.* 186, 5629-5639, doi:10.1128/jb.186.17.5629-5639.2004 (2004).

80 Qin, X., Singh, K. V., Weinstock, G. M. & Murray, B. E. Effects of *Enterococcus faecalis* fsr Genes on Production of Gelatinase and a Serine Protease and Virulence. doi: 10.1128/IAI.68.5.2579-2586.2000 (2000).

81 Thurlow, L. R. et al. Gelatinase contributes to the pathogenesis of endocarditis caused by *Enterococcus faecalis*. *Infect. Immun.* 78, 4936-4943, doi: 10.1128/iai.01118-09 (2010).

82 Engelbert, M., Mylonakis, E., Ausubel, F. M., Calderwood, S. B. & Gilmore, M. S. Contribution of gelatinase, serine protease, and fsr to the pathogenesis of *Enterococcus faecalis* endophthalmitis. *Infect. Immun.* 72, 3628-3633, doi: 10.1128/iai.72.6.3628-3633.2004 (2004).

83 Shankar, J., Walker, R. G., Ward, D. & Horsburgh, M. J. in *PLoS One* Vol. 7 (2012).

84 Darkoh, C., DuPont, H. L., Norris, S. J. & Kaplan, H. B. Toxin synthesis by *Clostridium difficile* is regulated through quorum signaling. *mBio* 6, e02569, doi:10.1128/mBio.02569-14 (2015).

85 Darkoh, C., Odo, C. & DuPont, H. L. Accessory Gene Regulator-1 Locus Is Essential for Virulence and Pathogenesis of *Clostridium difficile*. *mBio* 7, doi: 10.1128/mBio.01237-16 (2016).

86 Kuehne, S. A. et al. The role of toxin A and toxin B in *Clostridium difficile* infection. *Nature* 467, 711-713, doi: 10.1038/nature09397 (2010).

87 Cohen, S. H. et al. Clinical practice guidelines for *Clostridium difficile* infection in adults: 2010 update by the society for healthcare epidemiology of America (SHEA) and the infectious diseases society of America (IDSA). *Infect. Control Hosp. Epidemiol.* 31, 431-455, doi: 10.1086/651706 (2010).

88 Naskalska, A. & Pyre, K. Virus Like Particles as Immunogens and Universal Nanocarriers. *Pol. J. Microbiol.* 64, 3-13 (2015).

89 Lacson, E. et al. Antibody response to Engerix-B and Recombivax-HB hepatitis B vaccination in end-stage renal disease. *Hemodialysis international, International*

Symposium on Home Hemodialyis 9, 367-375, doi: 10.1111/j.1492-7535.2005.01155.x (2005).
90 GARDASIL®9 (Human Papillomavirus 9-valent Vaccine, Recombinant) for Health Care Professionals, <https://www.merckvacines.com/Products/Gardasil9 pgid=UoXun1CIyLRSR0EK44UuV0Tn0000rKPQB0Na sid=cz3-ITHtiBPkIWaMzyyb3i5Babw10BqEolE=> (2016).
91 Chackerian, B., Durfee, M. R. & Schiller, J. T. Virus-like display of a neo-self antigen reverses B cell anergy in a B cell receptor transgenic mouse model. J. Immunol 180, 5816-5825 (2008).
92 Chackerian, B., Lowy, D. R. & Schiller, J. T. Conjugation of a self-antigen to papillomavirus-like particles allows for efficient induction of protective autoantibodies. J. Clin. Invest 108, 415-423 (2001).
93 Chackerian, B., Lowy, D. R. & Schiller, J. T. Induction of autoantibodies to mouse CCR5 with recombinant papillomavirus particles. Proc. Natl. Acad. Sci. U.S.A 96, 2373-2378 (1999).
94 Frietze, K. M., Peabody, D. S. & Chackerian, B. Engineering virus-like particles as vaccine platforms. Curr. Opin. Virol. 18, 44-49, doi:10.1016/j.coviro.2016.03.001 (2016).
95 Effio, C. L. & Hubbuch, J. Next generation vaccines and vectors: Designing downstream processes for recombinant protein-based virus-like particles. Biotechnology journal 10, 715-727, doi:10.1002/biot.201400392 (2015).
96 Bachmann, M. F. & Jennings, G. T. Vaccine delivery: a matter of size, geometry, kinetics and molecular patterns. Nature reviews. Immunology 10, 787-796 (2010).
97 Jennings, G. T. & Bachmann, M. F. Immunodrugs: therapeutic VLP-based vaccines for chronic diseases. Annu. Rev. Pharmacol. Toxicol. 49, 303-326 (2009).
98 Rivera-Hernandez, T. et al. Self-adjuvanting modular virus-like particles for mucosal vaccination against group A streptococcus (GAS). Vaccine 31, 1950-1955, doi: 10.1016/j.vaccine.2013.02.013 (2013).
99 Seth, A. et al. Modular virus-like particles for sublingual vaccination against group A streptococcus. Vaccine, doi: 10.1016/j.vaccine.2016.11.008 (2016).
100 Tamborrini, M. et al. A Synthetic Virus-Like Particle Streptococcal Vaccine Candidate Using B-Cell Epitopes from the Proline-Rich Region of Pneumococcal Surface Protein A. Vaccines 3, 850-874, doi:10.3390/vaccines3040850 (2015).
101 Alksne, L. E. & Projan, S. J. Bacterial virulence as a target for antimicrobial chemotherapy. Curr. Opin. Biotechnol. 11, 625-636, doi:Doi 10.1016/S0958-1669(00) 00155-5 (2000).
102 in National Research Council (US) Committee for the Update of the Guide for iheCare and Use of Laboratory Animals (National Academies Press (US), 2011).
103 Rothfork, J. M., Dessus-Babus, S., Wamel, W. J. V., Cheung, A. L. & Gresham, H. D. Fibrinogen depletion attenuates Staphylococcus aureus infection by preventing density-dependent virulence gene up-regulation. J Immunol 171, 5389-5395 (2003).
104 Schneider, C. A., Rasband, W. S. & Eliceiri, K. W. NIH Image to ImageJ: 25 years of image analysis. Nat. Methods 9, 671-675 (2012).

What is claimed is:

1. A composition comprising: (a) a virus-like particle comprising a single chain dimer of PP7 or MS2 coat protein; and (b) at least one antigen or antigenic determinant according the sequence of SEQ ID NO:1, SEQ ID NO:2, SEQ ID NO:7, or SEQ ID NO:8 wherein said antigen or antigenic determinant is displayed on said virus-like particle at the A-B loop, N-terminus or carboxy terminus of said coat protein.

2. The composition according to claim 1 wherein said virus-like particle comprises a single chain dimer of PP7.

3. The composition according to claim 1 wherein said virus-like particle comprises a single chain dimer of PP7 and said antigen or antigenic determinant is according to the sequence of SEQ ID NO:1 or SEQ ID NO:2.

4. The composition according to claim 1 wherein said virus-like particle comprises a single chain dimer of PP7 and said antigen or antigenic determinant is according to the sequence of SEQ ID NO:1.

5. The composition according to claim 1 wherein said virus-like particle comprises a single chain dimer of PP7 and said antigen or antigenic determinant is according to the sequence of SEQ ID NO:2.

6. The composition according to claim 1 wherein said antigen or antigenic determinant is displayed on said virus-like particle at the A-B loop.

7. The composition according to claim 2 wherein said antigen or antigenic determinant is displayed on said virus-like particle at the A-B loop.

8. The composition according to claim 3 wherein said antigen or antigenic determinant is displayed on said virus-like particle at the A-B loop.

9. The composition according to claim 1 wherein said antigen or antigenic determinant is displayed on said virus-like particle at the N-terminus.

10. The composition according to claim 2 wherein said antigen or antigenic determinant is displayed on said virus-like particle at the N-terminus.

11. The composition according to claim 3 wherein said antigen or antigenic determinant is displayed on said virus-like particle at the N-terminus.

12. The composition according to claim 1 wherein said antigen or antigenic determinant is displayed on said virus-like particle at the carboxy terminus.

13. A population of virus-like particles according to claim 1.

14. A population of virus-like particles according to claim 3.

15. A population of virus-like particles according to claim 4.

16. A population of virus-like particles according to claim 5.

17. A pharmaceutical composition comprising a population of virus-like particles according to claim 13 in combination with a pharmaceutically acceptable carrier, additive and/or excipient.

18. A pharmaceutical composition comprising a population of virus-like particles according to claim 14 in combination with a pharmaceutically acceptable carrier, additive and/or excipient.

19. A pharmaceutical composition comprising a population of virus-like particles according to claim 15 in combination with a pharmaceutically acceptable carrier, additive and/or excipient.

20. A pharmaceutical composition comprising a population of virus-like particles according to claim 16 in combination with a pharmaceutically acceptable carrier, additive and/or excipient.

* * * * *